United States Patent [19]

Wareing

[11] Patent Number: 4,851,427

[45] Date of Patent: Jul. 25, 1989

[54] PYRROLE ANALOGS OF MEVALONOLACTONE, DERIVATIVES THEREOF AND PHARMACEUTICAL USE

[75] Inventor: James R. Wareing, Randolph, N.J.

[73] Assignee: Sandoz Pharm. Corp., E. Hanover, N.J.

[21] Appl. No.: 919,275

[22] Filed: Oct. 15, 1986

Related U.S. Application Data

[63] Continuation-in-part of Ser. No. 791,198, Oct. 25, 1985, abandoned.

[51] Int. Cl.⁴ .................. A61K 31/40; C07D 707/337; C07D 405/04; C07D 405/05
[52] U.S. Cl. ..................................... 514/422; 514/427; 548/517; 548/562
[58] Field of Search ................ 548/517, 562; 514/422, 514/427

[56] References Cited

U.S. PATENT DOCUMENTS

| | | | |
|---|---|---|---|
| 4,198,425 | 4/1980 | Mitsui et al. | 424/279 |
| 4,255,444 | 3/1981 | Oka et al. | 424/279 |
| 4,459,422 | 7/1984 | Willard et al. | 560/59 |
| 4,472,426 | 9/1984 | Hoffman et al. | 424/279 |
| 4,474,971 | 10/1984 | Wareing | 549/214 |
| 4,588,715 | 5/1986 | Damon | 514/63 |
| 4,613,610 | 9/1986 | Wareing | 514/406 |
| 4,647,576 | 3/1987 | Hoefle et al. | 514/422 |
| 4,681,893 | 7/1987 | Roth | 514/422 |

FOREIGN PATENT DOCUMENTS

| | | |
|---|---|---|
| 11928 | 6/1980 | European Pat. Off. . |
| 179559 | 4/1986 | European Pat. Off. . |
| 2261965 | 6/1973 | Fed. Rep. of Germany . |
| 84/02131 | 6/1984 | PCT Int'l Appl. . |
| 84/02903 | 8/1984 | PCT Int'l Appl. . |

OTHER PUBLICATIONS

Hoffman et al., J. Med. Chem., 29, 159–169, (1986).
Hulcher, Arch. Biochem. Biophys., 146, 422–427, (1971).
Sato et al., Chem. Pharm. Bull., (Tokyo), 28, 1509–1525, (1980).
Singer et al., Proc. Soc. Exper. Biol. Med., 102, 370–373, (1959).
Stokker et al., J. Med. Chem., 28, 347–358, (1985).
Stokker et al., J. Med. Chem., 29, 170–181, (1986).

Primary Examiner—Richard L. Raymond
Attorney, Agent, or Firm—Gerald D. Sharkin; Richard E. Vila; Melvyn M. Kassenoff

[57] ABSTRACT

Compounds of the formula

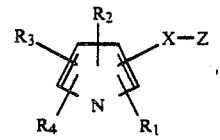

wherein $R_1$ is $C_{1-6}$alkyl not containing an asymmetric carbon atom, $C_{3-7}$cycloalkyl or

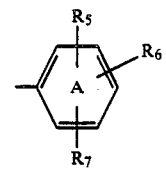

wherein $R_5$, $R_6$ and $R_7$ are as defined below,
$R_2$ is $C_{1-6}$alkyl not containing an asymmetric carbon atom, $C_{3-7}$cycloalkyl or

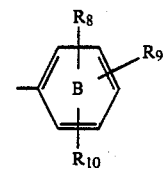

wherein $R_8$, $R_9$ and $R_{10}$ are as defined below.
$R_3$ is hydrogen, $C_{1-6}$alkyl not containing an asymmetric carbon atom, $C_{3-7}$cycloalkyl or

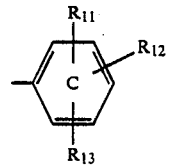

wherein $R_{11}$, $R_{12}$ and $R_{13}$ are as defined below,
$R_4$ is hydrogen, $C_{1-6}$alkyl not containing an asymmetric carbon atom, $C_{7-7}$cycloalkyl or

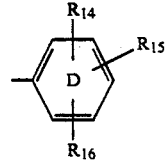

wherein $R_{14}$, $R_{15}$ and $R_{16}$ are as defined below,
X is —$(CH_2)_m$—, —CH=CH—, —CH=CH—$CH_2$— or —$CH_2$—CH=CH—, wherein m is 0, 1, 2 or 3, and
Z is (Abstract continued on next page.)

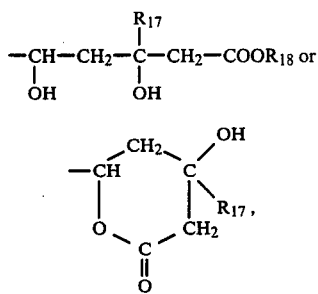

wherein $R_{17}$ is hydrogen or $C_{1-3}$alkyl, and
$R_{18}$ is hydrogen, $R_{19}$ or M, wherein $R_{19}$ is a physiologically acceptable ester group, and
M is a pharmaceutically acceptable cation, wherein each of $R_5$, $R_8$, $R_{11}$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_6$, $R_9$, $R_{12}$ and $R_{15}$ is independently hydrogen, $C_{1-3}$alkyl, $C_{1-3}$alkoxy, trifluoromethyl, fluoro, chloro, bromo, phenoxy or benzyloxy, and each of $R_7$, $R_{10}$, $R_{13}$ and $R_{16}$ is independently hydrogen, $C_{1-2}$alkyl, $C_{1-2}$alkoxy, fluoro or chloro, with the provisos that not more than one substituent on each of Rings A, B, C and D independently is trifluoromethyl, not more than one substituent on each of Rings A, B, C and D independently is phenoxy, and not more than one substituent on each of Rings A, B, C and D independently is benzyloxy, with the provisos that (i) the —X—Z group is in the 2- or 3-position of the pyrrole ring, (ii) the —X—Z group is ortho to both $R_1$ and $R_2$, and (iii) $R_3$ is ortho to $R_2$, the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

22 Claims, No Drawings

PYRROLE ANALOGS OF MEVALONOLACTONE, DERIVATIVES THEREOF AND PHARMACEUTICAL USE

This is a continuation-in-part of application Ser. No. 06/791,198, filed Oct. 25, 1985 and now abandoned.

This invention relates to compounds of the formula

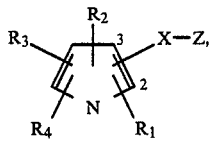
(I)

wherein $R_1$ is $C_{1-6}$alkyl not containing an asymmetric carbon atom, $C_{3-7}$cycloalkyl or

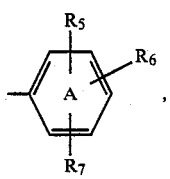

wherein $R_5$, $R_6$ and $R_7$ are as defined below, $R_2$ is $C_{1-6}$alkyl not containing an asymmetric carbon atom, $C_{3-7}$cycloalkyl or

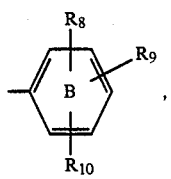

wherein $R_8$, $R_9$ and $R_{10}$ are as defined below, $R_3$ is hydrogen, $C_{1-6}$alkyl not containing an asymmetric carbon atom, $C_{3-7}$cycloalkyl or

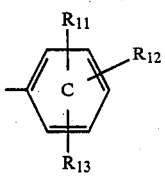

wherein $R_{11}$, $R_{12}$ and $R_{13}$ are as defined below, $R_4$ is hydrogen, $C_{1-6}$alkyl not containing an asymmetric carbon atom, $C_{3-7}$cycloalkyl or

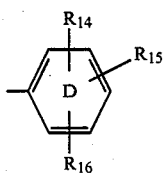

wherein $R_{14}$, $R_{15}$ and $R_{16}$ are as defined below,

X is $-(CH_2)_m-$, $-CH=CH-$, $-CH=CH-CH_2-$ or $-CH_2-CH=CH-$, wherein m is 0, 1, 2 or 3, and

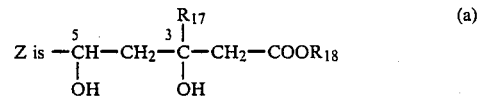
(a)

or

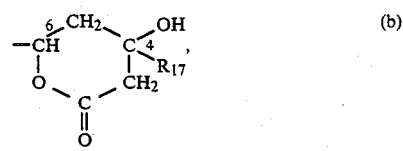
(b)

wherein $R_{17}$ is hydrogen or $C_{1-3}$alkyl, and $R_{18}$ is hydrogen, $R_{19}$ or M, wherein $R_{19}$ is a physiologically acceptable ester group, and M is a pharmaceutically acceptable cation, wherein each of $R_5$, $R_8$, $R_{11}$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_6$, $R_9$, $R_{12}$ and $R_{15}$ is independently hydrogen, $C_{1-3}$alkyl, $C_{1-3}$alkoxy, trifluoromethyl, fluoro, chloro, bromo, phenoxy or benzyloxy, and each of $R_7$, $R_{10}$, $R_{13}$ and $R_{16}$ is independently hydrogen, $C_{1-2}$alkyl, $C_{1-2}$alkoxy, fluoro or chloro, with the provisos that not more than one substituent on each of Rings A, B, C and D independently is trifluoromethyl, not more than one substituent on each of Rings A, B, C and D independently is phenoxy, and not more than one substituent on each of Rings A, B, C and D independently is benzyloxy, with the provisos that (i) the $-X-Z$ group is in the 2- or 3-position of the pyrrole ring, (ii) the $-X-Z$ group is ortho to both $R_1$ and $R_2$, and (iii) $R_3$ is ortho to $R_2$, processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable ester group" is meant a group which, together with the $-COO-$ radical to which it is attached, forms an ester group which is physiologically acceptable. The preferred such groups are the physiologically acceptable and hydrolyzable ester groups. By the term "physiologically acceptable and hydrolyzable ester group" is meant a group which, together with the $-COO-$ radical to which it is attached, forms an ester group which is physiologically acceptable and hydrolyzable under physiological conditions to yield a compound of Formula I wherein $R_{18}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_{19}'$.

For the avoidance of doubt, throughout this specification it is the right-hand side of the X radical that is attached to the Z group.

As is self-evident to those in the art, each compound of Formula I (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that $R_{18}$ does not contain any center of asymmetry. The four stereoisomers may be designated as the R,R, R,S, S,R and S,S enantiomers, all four stereoisomers being within the scope of this invention. When $R_{18}$ contains one or more centers of asymmetry, there are eight or more stereoisomers. Since it is preferred that $R_{18}$ not contain a center of asymmetry and for reasons of simplicity any additional stereoisomers resulting from the presence of one or more centers of asymmetry in $R_{18}$ usually will be ignored, it being assumed that $R_{18}$ is free of centers of asymmetry.

The compounds of Formula I may be divided into two groups, viz., those of Formulae IB and IC:

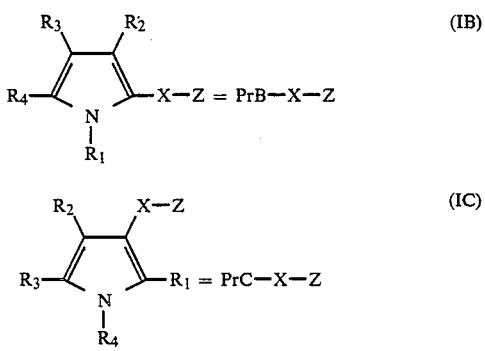

The compounds of each of Groups IB and IC may be divided into two subgroups based upon the significance of Z, viz., Group IBa (the compounds of Group IB wherein Z is a group of Formula a), Group IBb (the compounds of Group IB wherein Z is a group of Formula b), Group ICa (the compounds of Group IC wherein Z is a group of Formula a) and Group ICb (the compounds of Group IC wherein Z is a group of Formula b).

Preferably, one of $R_1$ and $R_2$ is $C_{1-6}$alkyl not containing an asymmetric carbon atom and the other is Ring A (if $R_1$) or Ring B (if $R_2$). Also preferably, one of $R_3$ and $R_4$ is Ring C (if $R_3$) or Ring D (if $R_4$) and the other is hydrogen or $C_{1-6}$alkyl not containing an asymmetric carbon atom, preferably hydrogen or $C_{1-2}$alkyl and most preferably hydrogen, except that $R_4$ in Formula IC is preferably other than hydrogen. More preferably, the preferences of both preceding sentences occur simultaneously. Thus, the preferred compounds of Formula I and each of the subscopes thereof are those having attached to the pyrrole ring (i) Ring A or Ring B, (ii) Ring C or Ring D, and (iii) two alkyl groups or, in the case of the compounds of Formula IB, especially one alkyl group and one hydrogen atom. Even more preferably, Ring A or Ring B, as the case may be; and Ring C or Ring D, as the case may be, are ortho to each other.

Also preferably, the pyrrole ring does not bear two ortho tertiary alkyl groups.

In Formula IB:

$R_1$ is preferably $R_{1Bx}$, where $R_{1Bx}$ is Ring A, more preferably $R_{1'Bx}$, where $R_{1'Bx}$ is Ring A wherein $R_5$ is $R_{5'}$, $R_6$ is $R_{6'}$, and $R_7$ is $R_{7'}$, even more preferably $R_{1''Bx}$, where $R_{1''Bx}$ is Ring A wherein $R_5$ is $R_{5''}$, $R_6$ is $R_{6''}$, and $R_7$ is hydrogen, and most preferably phenyl, 4-fluorophenyl or 3,5-dimethylphenyl, especially 4-fluorophenyl; or $R_1$ is preferably $R_{1By}$, where $R_{1By}$ is $C_{1-6}$alkyl not containing an asymmetric carbon atom, more preferably $R_{1'By}$, where $R_{1'By}$ is $C_{1-4}$alkyl not containing an asymmetric carbon atom, and most preferably i-propyl.

$R_2$ is preferably $R_{2Bx}$, where $R_{2Bx}$ is $C_{1-6}$alkyl not containing an asymmetric carbon atom, more preferably $R_{2'Bx}$, where $R_{2'Bx}$ is $C_{1-4}$alkyl not containing an asymmetric carbon atom, and most preferably i-propyl; or $R_2$ is preferably $R_{2By}$, where $R_{2By}$ is Ring B, more preferably $R_{2'By}$, where $R_{2'By}$ is Ring B wherein $R_8$ is $R_{8'}$, $R_9$ is $R_{9'}$, and $R_{10}$ is $R_{10'}$, even more preferably $R_{2''By}$, where $R_{2''By}$ is Ring B wherein $R_8$ is $R_{8''}$, $R_9$ is $R_{9''}$, and $R_{10}$ is hydrogen, and most preferably phenyl, 4-fluorophenyl or 3,5-dimethylphenyl, especially 4-fluorophenyl.

$R_3$ is preferably $R_{3Bx}$, where $R_{3Bx}$ is hydrogen or $C_{1-6}$alkyl not containing an asymmetric carbon atom, more preferably $R_{3'Bx}$, where $R_{3'Bx}$ is hydrogen or $C_{1-2}$alkyl, even more preferably $R_{3''Bx}$, where $R_{3''Bx}$ is hydrogen or methyl, and most preferably hydrogen; or $R_3$ is preferably $R_{3By}$, where $R_{3By}$ is Ring C, more preferably $R_{3'By}$, where $R_{3'By}$ is Ring C wherein $R_{11}$ is $R_{11'}$, $R_{12}$ is $R_{12'}$, and $R_{13}$ is $R_{13'}$, even more preferably $R_{3''By}$, where $R_{3''By}$ is Ring C wherein $R_{11}$ is $R_{11''}$, $R_{12}$ is $R_{12''}$, and $R_{13}$ is hydrogen, and most preferably phenyl.

$R_4$ is preferably $R_{4Bx}$, where $R_{4Bx}$ is Ring D, more preferably $R_{4'Bx}$, where $R_{4'Bx}$ is Ring D wherein $R_{14}$ is $R_{14'}$, $R_{15}$ is $R_{15'}$, and $R_{16}$ is $R_{16'}$, even more preferably $R_{4''Bx}$, where $R_{4''Bx}$ is Ring D wherein $R_{14}$ is $R_{14''}$, $R_{15}$ is $R_{15''}$, and $R_{16}$ is hydrogen, and most preferably phenyl; or $R_4$ is preferably $R_{4By}$, where $R_{4By}$ is hydrogen or $C_{1-6}$alkyl not containing an asymmetric carbon atom, more preferably $R_{4'By}$, where $R_{4'By}$ is hydrogen or $C_{1-2}$alkyl, even more preferably $R_{4''By}$, where $R_{4''By}$ is hydrogen or methyl, and most preferably hydrogen.

In Formula IC:

$R_1$ is preferably $R_{1Cx}$, where $R_{1Cx}$ is $C_{1-6}$alkyl not containing an asymmetric carbon atom, more preferably $R_{1'Cx}$, where $R_{1'Cx}$ is $C_{1-4}$alkyl not containing an asymmetric carbon atom, and most preferably i-propyl; or $R_1$ is preferably $R_{1Cy}$, where $R_{1Cy}$ is Ring A, more preferably $R_{1'Cy}$, where $R_{1'Cy}$ is Ring A wherein $R_5$ is $R_{5'}$, $R_6$ is $R_{6'}$, and $R_7$ is $R_{7'}$, even more preferably $R_{1''Cy}$, where $R_{1''Cy}$ is Ring A wherein $R_5$ is $R_{5''}$, $R_6$ is $R_{6''}$, and $R_7$ is hydrogen, and most preferably phenyl, 4-fluorophenyl or 3,5-dimethylphenyl, especially 4-fluorophenyl.

$R_2$ is preferably $R_{2Cx}$, where $R_{2Cx}$ is Ring B, more preferably $R_{2'Cx}$, where $R_{2'Cx}$ is Ring B wherein $R_8$ is $R_{8'}$, $R_9$ is $R_{9'}$, and $R_{10}$ is $R_{10'}$, even more preferably $R_{2''Cx}$, where $R_{2''Cx}$ is Ring B wherein $R_8$ is $R_{8''}$, $R_9$ is $R_{9''}$, and $R_{10}$ is hydrogen, and most preferably phenyl, 4-fluorophenyl or 3,5-dimethylphenyl, especially 4-fluorophenyl; or $R_2$ is preferably $R_{2Cy}$, where $R_{2Cy}$ is $C_{1-6}$alkyl not containing an asymmetric carbon atom, more preferably $R_{2'Cy}$, where $R_{2'Cy}$ is $C_{1-4}$alkyl not containing an asymmetric carbon atom, and most preferably i-propyl.

$R_3$ is preferably $R_{3Cx}$, where $R_{3Cx}$ is Ring C, more preferably $R_{3'Cx}$, where $R_{3'Cx}$ is Ring C wherein $R_{11}$ is $R_{11'}$, $R_{12}$ is $R_{12'}$, and $R_{13}$ is $R_{13'}$, even more preferably $R_{3''Cx}$, where $R_{3''Cx}$ is Ring C wherein $R_{11}$ is $R_{11''}$, $R_{12}$ is $R_{12''}$, and $R_{13}$ is hydrogen, and most preferably phenyl; or R$_3$ is preferably R$_{3Cy}$, where R$_{3Cy}$ is hydrogen or C$_{1-6}$alkyl not containing an asymmetric carbon atom, more preferably R$_3'_{Cy}$, where R$_3'_{Cy}$ is hydrogen or C$_{1-2}$alkyl, and even more preferably R$_3''_{Cy}$, where R$_3''_{Cy}$ is hydrogen or methyl, especially hydrogen.

R$_4$ is preferably R$_{4Cx}$, where R$_{4Cx}$ is hydrogen or C$_{1-6}$alkyl not containing an asymmetric carbon atom, more preferably R$_4'_{Cx}$, where R$_4'_{Cx}$ is C$_{1-2}$alkyl, and most preferably methyl; or R$_4$ is preferably R$_{4Cy}$, where R$_{4Cy}$ is Ring D, more preferably R$_4'_{Cy}$, where R$_4'_{Cy}$ is Ring D wherein R$_{14}$ is R$_{14}'$, R$_{15}$ is R$_{15}'$, and R$_{16}$ is R$_{16}'$, even more preferably R$_4''_{Cy}$, where R$_4''_{Cy}$ is Ring D wherein R$_{14}$ is R$_{14}''$, R$_{15}$ is R$_{15}''$, and R$_{16}$ is hydrogen, and most preferably phenyl.

In both formulae:

Each of R$_5$, R$_8$, R$_{11}$ and R$_{14}$ is preferably R$_5'$, R$_8'$, R$_{11}'$ and R$_{14}'$, respectively, where each of R$_5'$, R$_8'$, R$_{11}'$ and R$_{14}'$ is independently hydrogen, C$_{1-3}$alkyl, C$_{1-2}$alkoxy, trifluoromethyl, fluoro or chloro, and more preferably R$_5''$, R$_8''$, R$_{11}''$ and R$_{14}''$, respectively, where each of R$_5''$, R$_8''$, R$_{11}''$ and R$_{14}''$ is independently hydrogen, methyl or fluoro. R$_5''$ and R$_8''$ are most preferably fluoro, especially 4-fluoro, and R$_{11}''$ and R$_{14}''$ are most preferably hydrogen.

Each of R$_6$, R$_9$, R$_{12}$ and R$_{15}$ is preferably R$_6'$, R$_9'$, R$_{12}'$ and R$_{15}'$, respectively, where each of R$_6'$, R$_9'$, R$_{12}'$ and R$_{15}'$ is independently hydrogen, C$_{1-2}$alkyl, fluoro or chloro, more preferably R$_6''$, R$_9''$, R$_{12}''$ and R$_{15}''$, respectively, where each of R$_6''$, R$_9''$, R$_{12}''$ and R$_{15}''$ is independently hydrogen or methyl, and most preferably hydrogen.

Each of R$_7$, R$_{10}$, R$_{13}$ and R$_{16}$ is preferably R$_7'$, R$_{10}'$, R$_{13}'$ and R$_{16}'$, respectively, where each of R$_7'$, R$_{10}'$, R$_{13}'$ and R$_{16}'$ is independently hydrogen or methyl, and most preferably hydrogen.

Preferably, each of Rings A, B, C and D independently bears a maximum of one substituent selected from the group consisting of t-butyl, trifluoromethyl, phenyl, phenoxy and benzyloxy. More preferably, when any two or all three of the substituents on Ring A [R$_5$ (R$_5'$, etc.), R$_6$ (R$_6'$, etc.) and R$_7$ (R$_7'$, etc.)], Ring B [R$_8$ (R$_8'$, etc.), R$_9$ (R$_9'$, etc.) and R$_{10}$ (R$_{10}'$, etc.)], Ring C [R$_{11}$ (R$_{11}'$, etc.), R$_{12}$ (R$_{12}'$, etc.) and R$_{13}$ (R$_{13}'$, etc.)] and Ring D [R$_{14}$ (R$_{14}'$, etc.), R$_{15}$ (R$_{15}'$, etc.) and R$_{16}$ (R$_{16}'$, etc.)] independently are ortho to each other, at least one member of each pair that are ortho to each other is a member of the group consisting of hydrogen, methyl, methoxy, fluoro and chloro. Also more preferably, at least one of the ortho positions of each of Rings A, B, C and D independently has a member of the group consisting of hydrogen, fluoro and methyl.

Each of Rings A and B independently is preferably phenyl, 4-fluorophenyl or 3,5-dimethylphenyl, more preferably the latter two and most preferably 4-fluorophenyl.

Each of Rings C and D is preferably phenyl.

R$_{17}$ is preferably R$_{17}'$, where R$_{17}'$ is hydrogen or methyl, and most preferably hydrogen.

R$_{18}$ is preferably R$_{18}'$, where R$_{18}'$ is hydrogen, R$_{19}'$ or M, more preferably R$_{18}''$, where R$_{18}''$ is hydrogen, C$_{1-3}$alkyl or M, even more preferably R$_{18}'''$, where R$_{18}'''$ is hydrogen, C$_{1-2}$alkyl or M, and most preferably M, particularly M' and especially sodium.

R$_{19}$ is preferably a physiologically acceptable and hydrolyzable ester group, more preferably R$_{19}'$, where R$_{19}'$ is C$_{1-3}$alkyl, n-butyl, i-butyl, t-butyl or benzyl, even more preferably R$_{19}''$, where R$_{19}''$ is C$_{1-3}$alkyl, and most preferably R$_{19}'''$, where R$_{19}'''$ is C$_{1-2}$alkyl, especially ethyl.

Any —CH=CH—, —CH=CH—CH$_2$— or —CH$_2$—CH=CH— as X is preferably trans, i.e., (E).

X is preferably X', where X' is —CH$_2$CH$_2$— or —CH=CH—, and most preferably

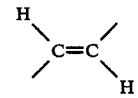

(i.e., (E) —CH=CH—).

Z is preferably a group of Formula a wherein R$_{17}$ is R$_{17}'$ (especially hydrogen), and R$_{18}$ is R$_{18}'$ or a group of Formula b wherein R$_{17}$ is R$_{17}'$ (especially hydrogen), more preferably a group of Formula a wherein R$_{17}$ is hydrogen, and R$_{18}$ is R$_{18}''$ or a group of Formula b wherein R$_{17}$ is hydrogen, even more preferably a group of Formula a wherein R$_{17}$ is hydrogen, and R$_{18}$ is R$_{18}'''$ or a group of Formula b wherein R$_{17}$ is hydrogen, and most preferably a group of Formula a wherein R$_{17}$ is hydrogen, and R$_{18}$ is M, preferably M' and especially sodium.

m is preferably m', where m' is 2 or 3, and most preferably 2.

M is preferably free from centers of asymmetry and is more preferably M', i.e., sodium, potassium or ammonium, and most preferably sodium. For simplicity, each formula in which M appears has been written as if M were monovalent and, preferably, it is. However, it may also be divalent or trivalent and, when it is, it balances the charge of two or three carboxy groups, respectively. Thus, Formula I and every other formula containing an M embraces compounds wherein M is divalent or trivalent, i.e., compounds containing two or three carboxylate-containing anions per cation M.

As between otherwise identical compounds of Formula I, those wherein Z is a group of Formula a are generally preferred over those wherein Z is a group of Formula b.

Insofar as the compounds of Groups IBa and ICa and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IBb and ICb and each of the subgroups thereof are concerned, the trans lactones are generally preferred over the cis lactones, cis and trans referring to the relative positions of R$_{17}$ and the hydrogen atom in the 6-position of the group of Formula b.

The preferred stereoisomers of the compounds of Formula I having only two centers of asymmetry wherein X is a direct bond, —CH=CH— or —CH$_2$—CH=CH—, and Z is a group of Formula a are the 3R,5S isomer and the racemate of which it is a constituent, i.e., the 3R,5S-3S,5R (erythro) racemate.

The preferred stereoisomers of the compounds of Formula I having only two centers of asymmetry wherein X is —CH$_2$—, —CH$_2$CH$_2$—, —CH$_2$CH$_2$CH$_2$— or —CH=CH—CH$_2$—, and Z is a group of Formula a are the 3R,5R isomer and the racemate of which it is a constituent, i.e., the 3R,5R-3S,5S (erythro) racemate.

The preferences set forth in the preceding two paragraphs also apply to the compounds of Formula I having more than two centers of asymmetry and represent the preferred configurations of the indicated positions.

The preferred stereoisomers of the compounds of Formula I wherein X is a direct bond, —CH=CH— or —CH$_2$—CH=CH—, and Z is a group of Formula b are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred.

The preferred stereoisomers of the compounds of Formula I wherein X is —CH$_2$—, —CH$_2$CH$_2$—, —CH$_2$CH$_2$CH$_2$— or —CH=CH—CH$_2$—, and Z is a group of Formula b are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred.

Each of the preferences set forth above applies, not only to the compounds of Formula I, but also to the compounds of Formulae IB and IC and those of Groups IBa, IBb, ICa and ICb as well as to every other subgroup thereof set forth in the specification, e.g., Groups (i) et seq., unless otherwise indicated. When any preference or group contains a variable, the preferred significances of that variable apply to the preference or group in question, unless otherwise indicated.

Preferred groups of compounds of Groups IBa, IBb, ICa and ICb include the compounds (i) of Group IBa wherein $R_1$ is $R_{1Bx}$, $R_2$ is $R_{2Bx}$, $R_3$ is $R_{3Bx}$, $R_4$ is $R_{4Bx}$, $R_{17}$ is $R_{17}'$, $R_{18}$ is $R_{18}'$, and X is X', (ii) of (i) wherein $R_1$ is $R_1'{}_{Bx}$, $R_2$ is $R_2'{}_{Bx}$, $R_3$ is $R_3'{}_{Bx}$, $R_4$ is $R_4'{}_{Bx}$, $R_{17}$ is hydrogen, $R_{18}$ is $R_{18}''$, and X is (E)—CH=CH—, (iii) of (ii) wherein $R_1$ is $R_1''{}_{Bx}$, $R_3$ is $R_3''{}_{Bx}$, $R_4$ is $R_4''{}_{Bx}$, and $R_{18}$ is $R_{18}'''$, preferably M, (iv) of Group IBa wherein $R_1$ is $R_{1By}$, $R_2$ is $R_{2By}$, $R_3$ is $R_{3By}$, $R_4$ is $R_{4By}$, $R_{17}$ is $R_{17}'$, $R_{18}$ is $R_{18}'$, and X is X', (v) of (iv) wherein $R_1$ is $R_1'{}_{By}$, $R_2$ is $R_2'{}_{By}$, $R_3$ is $R_3'{}_{By}$, $R_4$ is $R_4'{}_{By}$, $R_{17}$ is hydrogen, $R_{18}$ is $R_{18}''$, and X is (E)—CH=CH—, (vi) of (v) wherein $R_2$ is $R_2''{}_{By}$, $R_3$ is $R_3''{}_{By}$, $R_4$ is $R_4''{}_{By}$, and $R_{18}$ is $R_{18}'''$, preferably M, (vii) of Group IBa wherein $R_1$ is $R_{1By}$, $R_2$ is $R_{2By}$, $R_3$ is $R_{3Bx}$, $R_4$ is $R_{4Bx}$, $R_{17}$ is $R_{17}'$, $R_{18}$ is $R_{18}'$, and X is X', (viii) of (vii) wherein $R_1$ is $R_1'{}_{By}$, $R_2$ is $R_2'{}_{By}$, $R_3$ is $R_3'{}_{Bx}$, $R_4$ is $R_4'{}_{Bx}$, $R_{17}$ is hydrogen, $R_{18}$ is $R_{18}''$, and X is (E)—CH=CH—, (ix) of (viii) wherein $R_2$ is $R_2''{}_{By}$, $R_3$ is $R_3''{}_{Bx}$, $R_4$ is $R_4''{}_{Bx}$, and $R_{18}$ is $R_{18}'''$, preferably M, (x)-(xviii) of (i)-(ix) wherein the hydroxy groups in the 3- and 5-positions of the group of Formula a have the erythro configuration, (xix) of Group IBb wherein $R_1$ is $R_{1Bx}$, $R_2$ is $R_{2Bx}$, $R_3$ is $R_{3Bx}$, $R_4$ is $R_{4Bx}$, $R_{17}$ is $R_{17}'$, and X is X', (xx) of (xix) wherein $R_1$ is $R_1'{}_{Bx}$, $R_2$ is $R_2'{}_{Bx}$, $R_3$ is $R_3'{}_{Bx}$, $R_4$ is $R_4'{}_{Bx}$, $R_{17}$ is hydrogen, and X is (E)—CH=CH—, (xxi) of (xx) wherein $R_1$ is $R_1''{}_{Bx}$, $R_3$ is $R_3''{}_{Bx}$, and $R_4$ is $R_4''{}_{Bx}$, (xxii) of Group IBb wherein $R_1$ is $R_{1By}$, $R_2$ is $R_{2By}$, $R_3$ is $R_{3By}$, $R_4$ is $R_{4By}$, $R_{17}$ is $R_{17}'$, and X is X', (xxiii) of (xxii) wherein $R_1$ is $R_1'{}_{By}$, $R_2$ is $R_2'{}_{By}$, $R_3$ is $R_3'{}_{By}$, $R_4$ is $R_4'{}_{By}$, $R_{17}$ is hydrogen, and X is (E)—CH=CH—, (xxiv) of (xxiii) wherein $R_2$ is $R_2''{}_{By}$, $R_3$ is $R_3''{}_{By}$, and $R_4$ is $R_4''{}_{By}$, (xxv) of Group IBb wherein $R_1$ is $R_{1By}$, $R_2$ is $R_{2By}$, $R_3$ is $R_{3Bx}$, $R_4$ is $R_{4Bx}$, $R_{17}$ is $R_{17}'$, and X is X', (xxvi) of (xxv) wherein $R_1$ is $R_1'{}_{By}$, $R_2$ is $R_2'{}_{By}$, $R_3$ is $R_3'{}_{Bx}$, $R_4$ is $R_4'{}_{Bx}$, $R_{17}$ is hydrogen, and X is (E)—CH=CH—, (xxvii) of (xxvi) wherein $R_2$ is $R_2''{}_{By}$, $R_3$ is $R_3''{}_{Bx}$, and $R_4$ is $R_4''{}_{Bx}$, (xxviii)-(xxxvi) of (xix)-(xxvii) wherein $R_{17}$ and the hydrogen atom in the 6-position of the group of Formula b are trans to each other, i.e., the trans lactones, (xxxvii) of Group ICa wherein $R_1$ is $R_{1Cx}$, $R_2$ is $R_{2Cx}$, $R_3$ is $R_{3Cx}$, $R_4$ is $R_{4Cx}$, $R_{17}$ is $R_{17}'$, $R_{18}$ is $R_{18}'$, and X is X', (xxxviii) of (xxxvii) wherein $R_1$ is $R_1'{}_{Cx}$, $R_2$ is $R_2'{}_{Cx}$, $R_3$ is $R_3'{}_{Cx}$, $R_4$ is $R_4'{}_{Cx}$, $R_{17}$ is hydrogen, $R_{18}$ is $R_{18}''$, and X is (E)—CH=CH—, (xxxix) of (xxxviii) wherein $R_2$ is $R_2''{}_{Cx}$, $R_3$ is $R_3''{}_{Cx}$, $R_4$ is methyl, and $R_{18}$ is $R_{18}'''$, preferably M, (xl) of Group ICa wherein $R_1$ is $R_{1Cy}$, $R_2$ is $R_{2Cy}$, $R_3$ is $R_{3Cy}$, $R_4$ is $R_{4Cy}$, $R_{17}$ is $R_{17}'$, $R_{18}$ is $R_{18}'$, and X is X', (xli) of (xl) wherein $R_1$ is $R_1'{}_{Cy}$, $R_2$ is $R_2'{}_{Cy}$, $R_3$ is $R_3'{}_{Cy}$, $R_4$ is $R_4'{}_{Cy}$, $R_{17}$ is hydrogen, $R_{18}$ is $R_{18}''$, and X is (E)—CH=CH—, (xlii) of (xli) wherein $R_1$ is $R_1''{}_{Cy}$, $R_3$ is $R_3''{}_{Cy}$, $R_4$ is $R_4''{}_{Cy}$, and $R_{18}$ is $R_{18}'''$, preferably M, (xliii)-(xlviii) of (xxxvii)-(xlii) wherein the hydroxy groups in the 3- and 5-positions of the group of Formula a have the erythro configuration, (xlix) of Group ICb wherein $R_1$ is $R_{1Cx}$, $R_2$ is $R_{2Cx}$, $R_3$ is $R_{3Cx}$, $R_4$ is $R_{4Cx}$, $R_{17}$ is $R_{17}'$, and X is X', (l) of (xlix) wherein $R_1$ is $R_1'{}_{Cx}$, $R_2$ is $R_2'{}_{Cx}$, $R_3$ is $R_3'{}_{Cx}$, $R_4$ is $R_4'{}_{Cx}$, $R_{17}$ is hydrogen, and X is (E)—CH=CH—, (li) of (l) wherein $R_2$ is $R_2''{}_{Cx}$, $R_3$ is $R_3''{}_{Cx}$, and $R_4$ is methyl, (lii) of Group ICb wherein $R_1$ is $R_{1Cy}$, $R_2$ is $R_{2Cy}$, $R_3$ is $R_{3Cy}$, $R_4$ is $R_{4Cy}$, $R_{17}$ is $R_{17}'$, and X is X', (liii) of (lii) wherein $R_1$ is $R_1'{}_{Cy}$, $R_2$ is $R_2'{}_{Cy}$, $R_3$ is $R_3'{}_{Cy}$, $R_4$ is $R_4'{}_{Cy}$, $R_{17}$ is hydrogen, and X is (E)—CH=CH—, (liv) of (liii) wherein $R_1$ is $R_1''{}_{Cy}$, $R_3$ is $R_3''{}_{Cy}$, and $R_4$ is $R_4''{}_{Cy}$, and (lv)-(lx) of (xlix)-(liv) wherein $R_{17}$ and the hydrogen atom in the 6-position of the group of Formula b are trans to each other, i.e., the trans lactones.

Groups (x)-(xviii) and (xliii)-(xlviii) embrace the 3R,5S-3S,5R racemate and the 3R,5S and 3S,5R enantiomers of the compounds wherein X is —CH=CH—, the 3S,5R enantiomer being least preferred, and the 3R,5R-3S,5S racemate and the 3R,5R and 3S,5S enantiomers of the compounds wherein X is —CH$_2$CH$_2$—, the 3S,5S enantiomer being least preferred.

Groups (xxviii)-(xxxvi) and (lv)-(lx) embrace the 4R,6S-4S,6R racemate and the 4R,6S and 4S,6R enantiomers of the compounds wherein X is —CH=CH—, the 4S,6R enantiomer being least preferred, and the 4R,6R-4S,6S racemate and the 4R,6R and 4S,6S enantiomers of the compounds wherein X is —CH$_2$CH$_2$—, the 4S,6S enantiomer being least preferred.

Other representative groups of compounds are (1)-(3) those of Formulae I, IB and IC wherein each of $R_6$, $R_9$, $R_{12}$ and $R_{15}$ is other than bromo and (4)-(23) those of Groups (i), (iv), (vii), (x), (xiii), (xvi), (xix), (xxii), (xxv), (xxviii), (xxxi), (xxxiv), (xxxvii), (xl), (xliii), (xlvi), (xlix), (lii), (lv) and (lviii) wherein each of $R_6$, $R_9$, $R_{12}$ and $R_{15}$ is other than bromo.

The compounds of Formula I may be synthesized as follows:

and $R_{18}$ is $M_2^{\oplus}$ or $R_{20}$ may be synthesized by the following series of reactions:

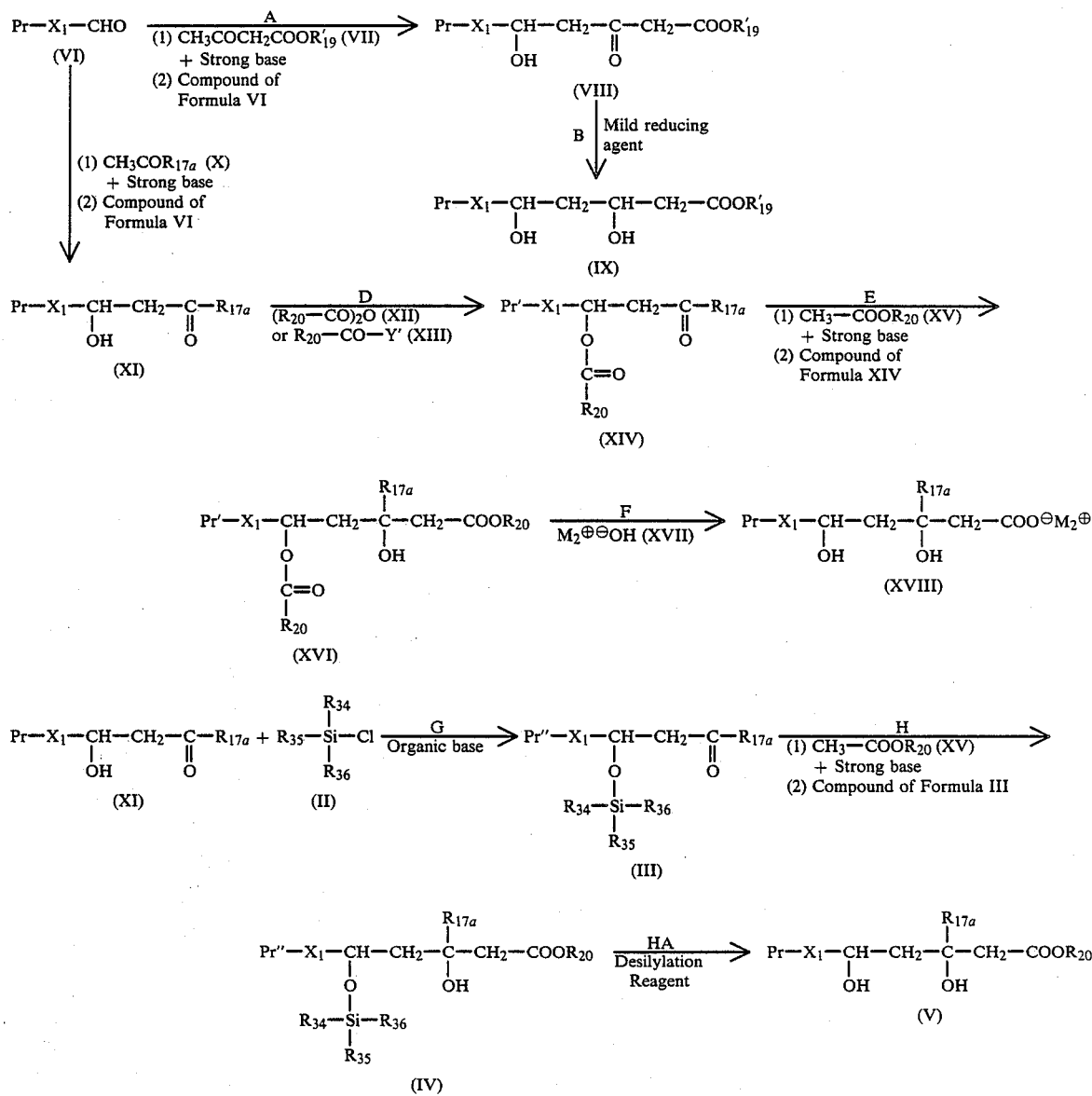

Reaction Scheme I

The compounds of Formula I wherein X is $-(CH_2)_m-$ or $(E)-CH=CH-$, and Z is a group of Formula a wherein $R_{17}$ is hydrogen, and $R_{18}$ is $R_{19}'$ or $R_{17}$ is $R_{17a}$

Reaction Scheme II

The compounds of Formula I wherein X is $-CH_2CH_2-$, $-CH_2CH_2CH_2-$, $-CH=CH-$, $-CH=CH-CH_2-$ or $-CH_2-CH=CH-$, and Z is a group of Formula a wherein $R_{18}$ is $R_{19}'$ may be synthesized by the following series of reactions:

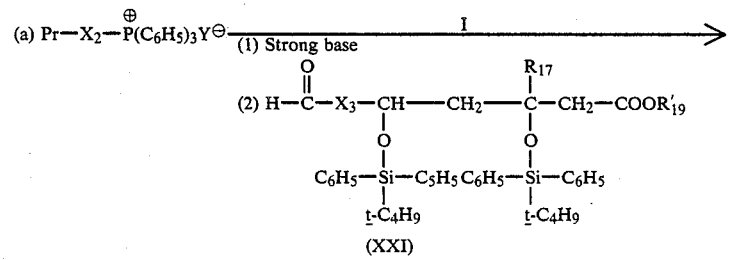

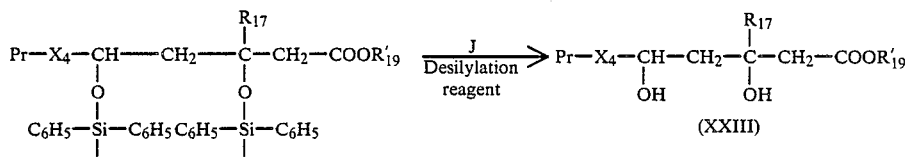

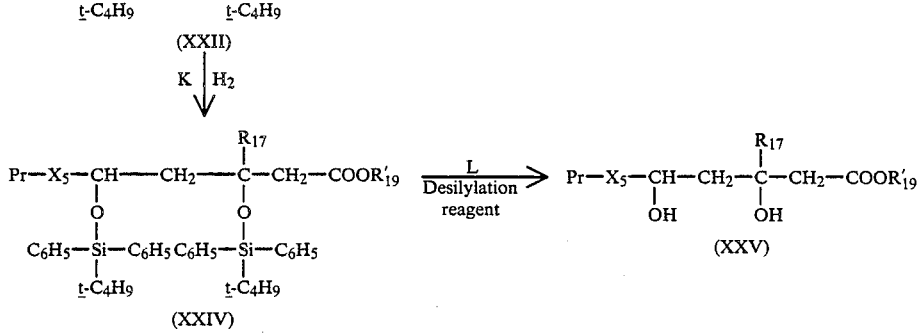

Reaction Scheme III

The compounds of Formula I wherein X is —CH═CH— or —CH₂—CH═CH—, and Z is a group of Formula b having the 4R,6S configuration or X is —CH₂CH₂— or —CH₂CH₂CH₂—, and Z is a group of Formula b having the 4R,6R configuration may be synthesized by the following series of reactions:

Reaction Scheme IV

The compounds of Formula I wherein Z is a group of Formula a wherein $R_{18}$ is $R_{19}'$ or a group of Formula b may be converted into the corresponding compounds of Formula I wherein Z has a different significance by the following series of reactions:

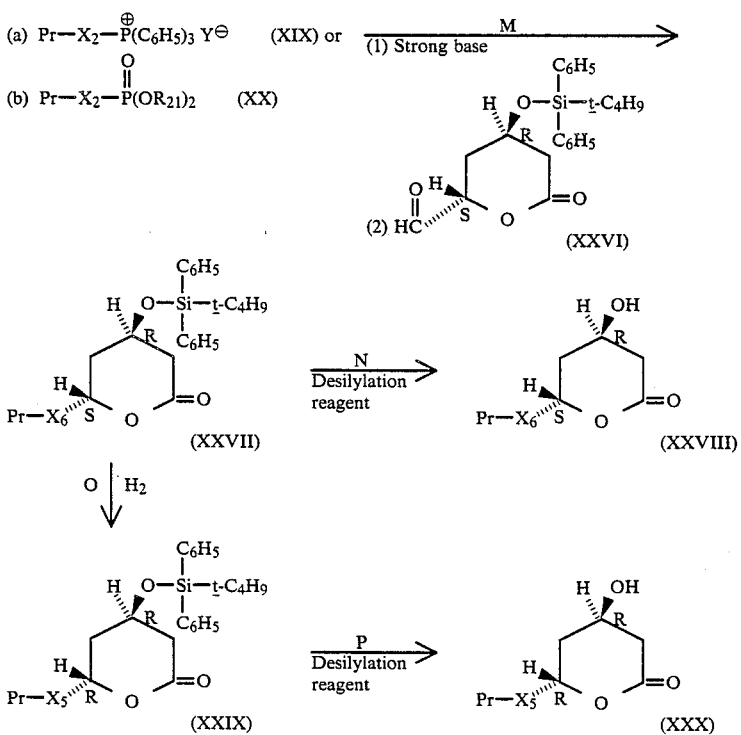

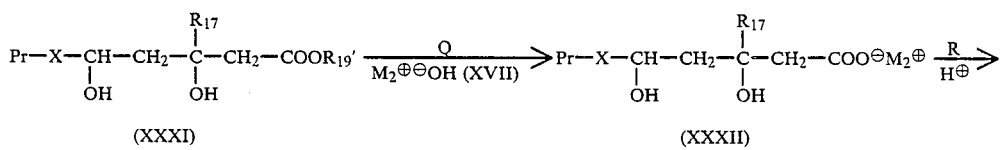

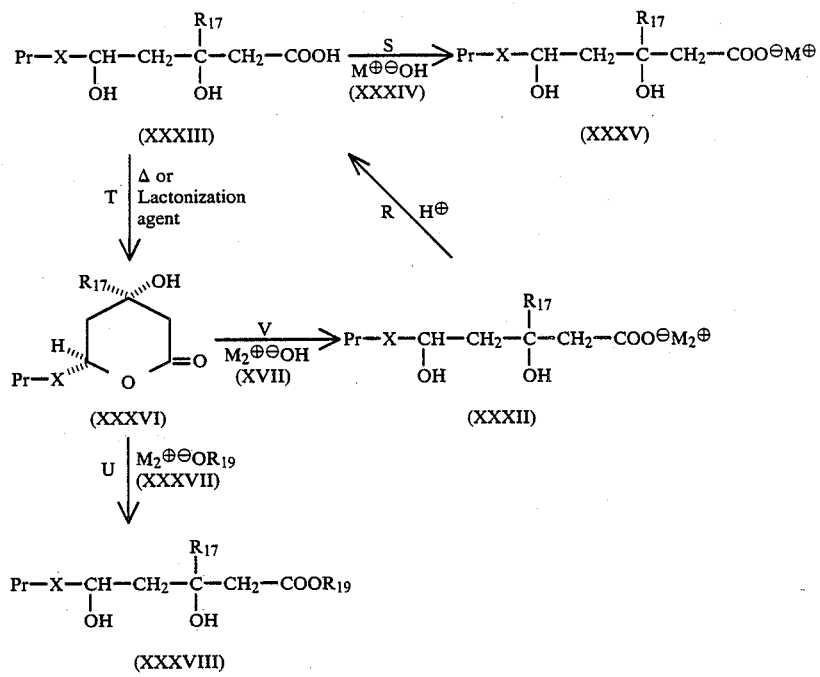
Reaction Scheme V
The compounds of Formula VI may be synthesized by the following series of reactions:
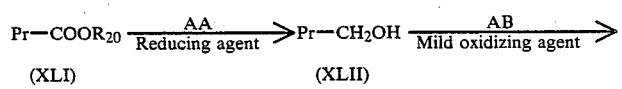
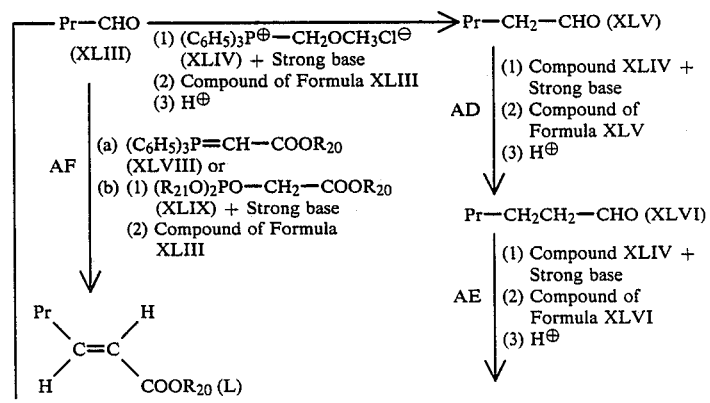

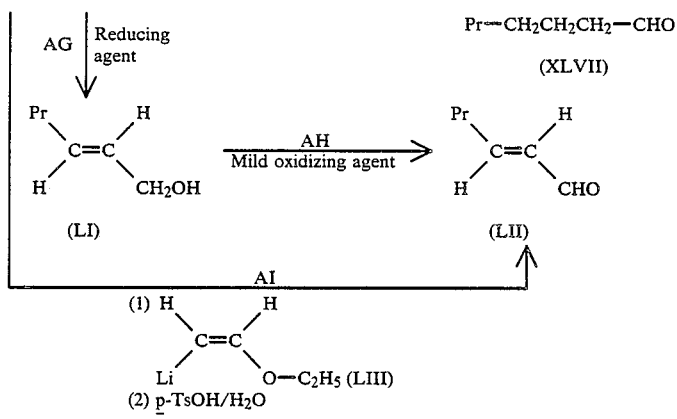
Reaction Scheme VI
The compounds of Formulae XIX and XX may be synthesized by the following series of reactions:
Reaction Scheme VII
The compounds of Formula XLI wherein Pr is PrB wherein $R_4$ is $R_{4a}$ may be synthesized by the following series of reactions:
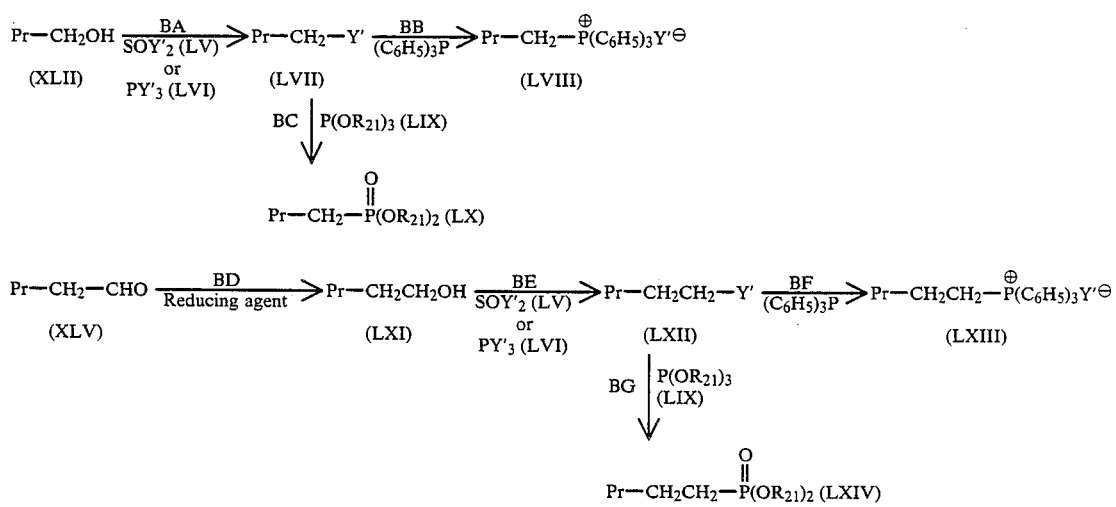
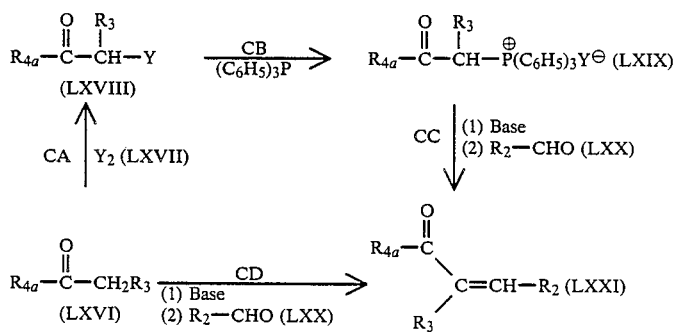

-continued

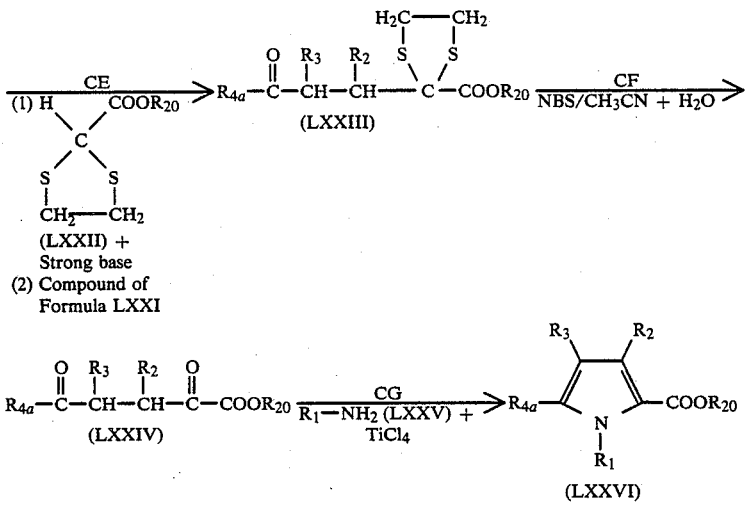

(LXXII) +
Strong base
(2) Compound of Formula LXXI

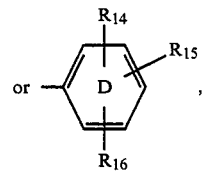

In the preceding reaction schemes,

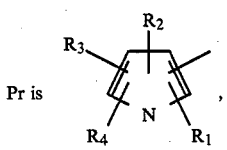

Pr is wherein $R_1$-$R_4$ are as defined above,

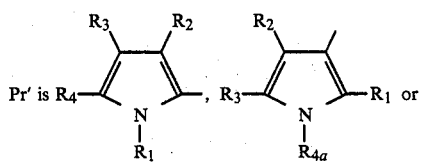

Pr' is

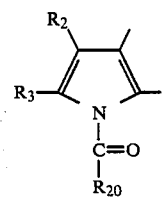

wherein $R_1$-$R_4$ are as defined above, and $R_{4a}$ and $R_{20}$ are as defined below,

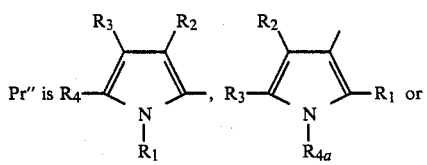

Pr'' is

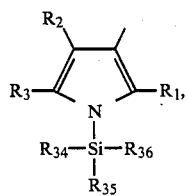

wherein $R_1$-$R_4$ as as defined above, and $R_{4a}$ and $R_{34}$-$R_{36}$ are as defined below, $R_{4a}$ is $C_{1-6}$alkyl not containing an asymmetric carbon atom, $C_{3-7}$cycloalkyl or wherein $R_{14}$-$R_{16}$ are as defined above, $R_{17a}$ is $C_{1-3}$alkyl, each $R_{20}$ is independently $C_{1-3}$alkyl, preferably n-$C_{1-3}$alkyl, and most preferably $C_{1-2}$alkyl, each $R_{21}$ is independently $C_{1-2}$alkyl, the two $C_{1-2}$alkyl groups preferably being the same, each of $R_{34}$ and $R_{35}$ is independently $C_{1-6}$alkyl not containing an asymmetric carbon atom, preferably methyl, $R_{36}$ is $C_{1-6}$alkyl not containing an asymmetric carbon atom, preferably methyl or t-butyl and especially t-butyl, $X_1$ is —(CH$_2$)$_m$— or (E)—CH=CH—, especially (E)—CH=CH—, wherein m is 0, 1, 2 or 3, $X_2$ is —CH$_2$— or —CH$_2$CH$_2$—, $X_3$ is a direct bond or —CH$_2$—, $X_4$ is —CH$_2$—, —CH=CH—, —CH=CH—CH$_2$— or —CH$_2$—CH=CH—, preferably (E)—CH=CH—, (E)—CH=CH—CH$_2$— or (E)—CH$_2$—CH=CH— and especially (E)—CH=CH—, $X_5$ is —CH$_2$CH$_2$— or —CH$_2$CH$_2$CH$_2$—, especially —CH$_2$CH$_2$—, $X_6$ is —CH=CH— or —CH$_2$—CH=CH—, preferably —CH=CH— and especially (E)—CH=CH—, Y is chloro, bromo or iodo, $Y^\ominus$ is chloride, bromide or iodide, Y' is chloro or bromo, $Y'^\ominus$ is chloride or bromide, $M_2^\oplus$ is sodium or potassium, and each of the other variables is as defined above.

| Reaction/Type | Reagents, Molar Ratios and Comments | Temperature | Time | Solvent | Inert Atmosphere |
|---|---|---|---|---|---|
| A | (1) Generation of dianion of VII: 2–2.4 equivalents strong base, pref. 1–1.1 moles sodium hydride then 1–1.1 moles n-butyllithium or 2–2.2 moles lithium diisopropylamide per mole VII. | −50°–10° C., pref. −20°–5° C. | 0.5–3 hrs. | AIO, e.g., ES, pref. THF | Yes (pref. argon) |
|  | (2) 1–2.5 moles, pref. 1.2–2.2 moles, more pref. 1.3–2.1 moles, dianion of VII (assuming 100% conversion of VII to its dianion) per mole VI. When Pr is PrC wherein R$_4$ is hydrogen, use extra equivalent of dianion, i.e., 2–3.5 moles, pref. 2.2–3.2 moles and more pref. 2.3–3.1 moles, per mole VI. | −80°–0° C., pref. −50°–0° C., more pref. −30°– −10° C. | 0.2–4 hrs., pref. 0.3–2.5 hrs. | Same as Step 1 | Yes (pref. argon) |
|  | (3) Quench with, e.g., saturated ammonium chloride solution. Product (VIII) is racemic. | Same as Step 2 | 1–5 min. | Same as Step 1 | — |
| B (Reduction) | (a) Non-stereoselective: 1–4, pref. 2–4, equivalents transferable hydride per mole VIII, pref. sodium borohydride or complex of t-butylamine and borane. When a racemic VIII is utilized, product (IX) is a mixture of all four possible stereoisomers (the erythro and threo racemates) wherein the ratio of the erythro stereoisomers to the threo stereoisomers is about 3:2–2:3. (b) Stereoselective: | −10°–30° C. | 1–8 hrs. | IO, e.g., lower alkanol, esp. ethanol | Yes |
|  | (1) 1–2.2 moles, pref. 1.02–2 moles, tri-(primary or secondary C$_{2-4}$ alkyl)-borane, pref. triethylborane or tri-n-butylborane, and, optionally, air, e.g., 0.5–8 l., pref. 0.75–6.5 l., (at 25° C. and 760 mm. Hg.) per mole VIII. | 0°–50° C., pref. 0°–25° C. | 0.5–6 hrs., pref. 1–3.5 hrs. | AIO, pref. ES, esp. THF, or mixture of THF and methanol, pref. a 3–4:1 mixture | Pref. Yes |
|  | (2) 0.4–10 moles, pref. 1–10 moles, sodium borohydride per mole VIII. After the reaction, quench reaction mixture with, for example, 10% hydrochloric acid and isolate crude product by extracting with a suitable inert organic solvent (e.g., diethyl ether) and evaporating the solvent at reduced pressure. It is pref. to crystallize the cyclic boron ester, if possible. It may be necessary to complete the reaction at −50°– −10° C. | −100°– −10° C., pref. −90°– −70° C. | 1–96 hrs., pref. 12–72 hrs. | Same as Step 1 | Pref. Yes |
|  | (3) Large excess of anhydrous methanol, e.g., 50–100 moles per mole VIII. It is convenient to azeotrope a solution of the product of Step 2 in methanol three to four times. When a racemic VIII is utilized in Alternative b, product (IX) is a mixture of the four possible stereoisomers wherein the ratio of the erythro isomers (racemate) to the threo isomers (racemate) is about 2–20:1, usually 5–15:1, when the solvent is THF. Repeated recrystallization of the cyclic boron ester produced in Step 2 of Alternative b, if a solid, may raise the ratio or even yield pure erythro racemate and mother liquors enriched with threo racemate. When, however, the solvent is a mixture of THF and methanol, said ratio may be as high as 50–100:1. | 20°–60° C. | 0.5–5 hrs., pref. 1–4 hrs. | Neat | — |
| C | (1) Generation of monoanion of X: 1–1.1 equivalents strong base, pref. lithium diisopropylamide, per mole X. | −80°– −40° C., pref. −80°– −75° C. | 0.25–1.5 hrs. | AIO, e.g., ES, pref. THF | Yes |
|  | (2) 1–4 moles, pref. 3 moles, monoanion of X (assuming 100% conversion of X to its monoanion) per mole VI. When Pr is PrC wherein R$_4$ is hydrogen, use extra equivalent of monoanion, i.e., 2–5 moles, pref. 4 moles, monoanion per mole VI. | −80°– −40° C., pref. −80°– −75° C. | 0.25–1.5 hrs. | Same as Step 1 | Yes |
|  | (3) Quench with, for example, saturated ammonium chloride solution. Product (XI) is a racemate. | −80°–25° C. | 1–5 min. | — | — |
| D (Acylation) | 1–3 moles, pref. 2 moles, XII or XIII per mole XI. When an ES is used as the solvent, | −10°–50° C., pref. 20°–30° C. | 2–18 hrs., pref. 4–12 | Pyridine or anhydrous ES, | Yes |

-continued

| Reaction/Type | Reagents, Molar Ratios and Comments | Temperature | Time | Solvent | Inert Atmosphere |
|---|---|---|---|---|---|
| | also use 1-4 moles, pref. 2.5-3 moles, of a tertiary amine, e.g., pyridine or, pref., 4-dimethylaminopyridine, per mole XI. When Pr is PrC wherein $R_4$ is hydrogen, use extra equivalent of XII or XIII and tertiary amine (when used), e.g., 2-4 moles, pref. 3 moles, XII or XIII per mole XI. Always use at least one mole of tertiary amine (when used) per mole XII or XIII. | | hrs. | pref. THF | |
| E | (1) Generation of monoanion of XV: 1-1.1 equivalents strong base, pref. lithium diisopropylamide, per mole XV. | $-80°-0°$ C. | 0.25-1 hr. | AIO, e.g., ES, pref. THF | Yes |
| | (2) 1-4 moles, pref. 3 moles, monoanion of XV (assuming 100% conversion of XV to its monoanion) per mole XIV. | $-80°- -40°$ C., pref. $-80°- -70°$ C. | 0.25-1.5 hrs. | Same as Step 1 | Yes |
| | (3) Quench with, for example, saturated ammonium chloride solution. | $-80°-25°$ C. | 1-5 min. | — | — |
| F (Hydrolysis) | 2-2.3 moles, pref. 2-2.2 moles, XVII per mole XVI. When Pr' contains an $R_{20}$—CO- group, utilize at least one additional equivalent of XVII, e.g., 3-3.3 moles, pref. 3-3.2 moles, XVII per mole XVI. | 20° C.-reflux, pref. 20°-75° C., esp. 50°-75° C., when Pr' contains an $R_{20}$—CO- group and, otherwise, 0° C.-reflux, pref. 0°-75° C., esp. 20°-50° C. | 2-12 hrs. when Pr' contains an $R_{20}$—CO- group and, otherwise, 1-4 hrs. | Inert aqueous organic, e.g., mixture of water and lower alkanol, pref. mixture of water and methanol or, esp., ethanol | — |
| G (Silylation) | 1-3 moles II per mole XI. When Pr is PrC wherein $R_4$ is hydrogen, use at least one extra equivalent of II, e.g., 2-4 moles II per mole XI. In either case, also use 1-2 moles triethylamine and catalytic amount of imidazole or 1.1-2 moles imidazole per mole II. | 20°-30° C., pref. 20°-25° C. | 6-18 hrs. | Dry dimethylformamide | Yes |
| H | Same as Reaction E (Molar quantities in Step 2 are per mole III). | Same as E | Same as E | Same as E | Yes |
| HA (Deprotection) | Same as Reaction J (Molar quantities are per mole IV) when Pr" contains an —$SiR_{34}R_{35}R_{36}$ group. When Pr" does not contain an —$SiR_{34}R_{35}R_{36}$ group, utilize 1-4 moles, pref. 2-4 moles, fluoride reagent per mole IV. | Same as J | Same as J | Same as J | — |
| I (Wittig) | Alternative a: (1) 1-2 moles strong base, e.g., sodium hydride or pref. n-butyllithium, per mole XIX. Pref., slowly add n-butyllithium solution to solution of XIX. When Pr is PrC wherein $R_4$ is hydrogen, use 2-3 moles strong base per mole XIX. | $-40°-5°$ C., pref. $-35°- -20°$ C. | 5-60 min. | AIO, e.g., HC such as toluene or, pref., ES such as THF | Yes |
| | (2) 0.65-1.5 moles XXI per mole XIX used in Step 1. | $-55°-25°$ C., pref. $-35°- -5°$ C. | 0.75-18 hrs., pref. 1-4 hrs. | Same as Step 1 | Yes |
| M (Wittig) | Same as Reaction I. (Reactant in Step 2 is XXVI). Product (XXVII) is a mixture of the (Z) and (E) (cis and trans, respectively) isomers which may be separated by chromatography. The (E) to (Z) ratio may be higher with Alternative b than with Alternative a. | Same as I | Same as I | Same as I | Yes |
| N (Deprotection) | Same as Reaction J except utilize 1-4 moles, pref. 2-4 moles, fluoride reagent per mole XXVII. | Same as J | Same as J | Same as J | — |
| O (Hydrogenation) | Same as Reaction K (Molar quantities are per mole XXVII). | Same as K | Same as K | Same as K | — |
| P (Deprotection) | Same as Reaction J except utilize 1-4 moles, pref. 2-4 moles, fluoride reagent per mole XXIX. | Same as J | Same as J | Same as J | — |
| Q (Hydrolysis) | 1-1.3 equivalents XVII per mole XXXI or, if it is desired to isolate XXXII, 0.92-0.99 equivalent XVII per mole XXXI. | 0° C.-reflux, pref. 0°-75° C., esp. 20°-70° C. | 1-4 hrs. | Inert aqueous organic, e.g., mixture of water and lower alkanol, pref. mixture of water and methanol or, esp., ethanol | — |
| R (Acidification) | At least 1 equivalent, e.g., 1-1.25 equivalents, acid, e.g., 2N. hydrochloric acid, per mole XXXII. | 0°-25° C. | 1-5 min. | Water or mixture of water and water-miscible or partially | |

-continued

| Reaction/Type | Reagents, Molar Ratios and Comments | Temperature | Time | Solvent | Inert Atmosphere |
|---|---|---|---|---|---|
| | | | | miscible inert organic solvent, e.g., methanol, ethanol, diethyl ether or THF | |
| S (Neutralization) | 0.95–0.99 equivalent, pref. 0.96–0.98 equivalent, XXXIV per mole XXXIII. | 0°–25° C., pref. 20°–25° C. | 2–10 min. | Same as Q | — |
| T (Lactonization) | Alternative a: Use of catalytic amount of strong acid such as p-toluenesulfonic acid is optional but usually omit. Use of Dean-Stark apparatus is pref. if solvent forms azeotrope with water. | 75° C.-reflux, pref. 75°– 150° C., esp. 80°–120° C. | 3–18 hrs., pref. 4–7 hrs. | AIO, pref. HC, e.g., benzene, toluene or xylene or mixture thereof | |
| | Alternative b: 1–1.5 moles of a lactonization agent, e.g., a carbodiimide, pref. a water-soluble carbodiimide such as N—cyclohexyl-N'—[2'-(N"—methylmorpholinium)-ethyl] carbodiimide p-toluenesulfonate, per mole XXXIII. Alternative b often results in higher yields of XXXVI than Alternative a. Racemic erythro XXXIII yields racemic trans (lactone) XXXVI, racemic threo XXXIII yields racemic cis (lactone) XXXVI, mixture of racemic erythro and threo XXXIII yields mixture of racemic trans and cis (lactones) XXXVI, and single enantiomer of XXXIII yields single enantiomer of XXXVI, e.g., 3R,5S erythro XXXIII yields 4R,6S trans XXXVI. | 10°–35° C., pref. 20°–25° C. | 2–8 hrs., pref. 3–4 hrs. | AIO, pref. HLA, esp. methylene chloride | |
| U (Esterification) | At least 2 moles, e.g., 2–10 moles, pref. 2.05–2.5 moles, XXXVII per mole XXXVI. See comment concerning Reaction V, this column. | 0°–70° C., pref. 20°–25° C. | 2–12 hrs. | IO, e.g., ES such as THF or alcohol of the formula $R_{19}$-OH ($R_{19}$ same as in XXXVII), if a liquid | — |
| V (Hydrolysis) | 1–1.3 equivalents XVII per mole XXXVI or, if it is desired to isolate XXXII, 0.95–1 equivalent, preferably 0.97–0.99 equivalent, XVII per mole XXXVI. Racemic trans (lactone) XXXVI yields racemic erythro XXXII or XXXVIII, racemic cis (lactone) XXXVI yields racemic threo XXXII or XXXVIII, mixture of racemic trans and cis (lactones) XXXVI yields mixture of racemic erythro and threo XXXII or XXXVIII, and single enantiomer of XXXVI yields single enantiomer of XXXII or XXXVIII, e.g., 4R,6S trans XXXVI yields 3R,5S erythro XXXII or XXXVIII. | 0° C.-reflux, pref. 0°–75° C., more pref. 20°– 75° C., esp. 40°– 60° C. | 1–6 hrs., pref. 1–4 hrs. | Same as Q | — |
| AA (Reduction) | 0.5–3.2 moles, pref. 0.75–3 moles, lithium aluminum hydride per mole XLI. Pref. commence at −5°–5° C. and allow reaction mixture to warm to 20°–25° C. as reaction proceeds or run entire reaction at 0°–5° C. | −5°–25° C., pref. −5°–5° C.→ 20°–25° C. or 0°–5° C. | 2–6 hrs., pref. 2–4 hrs. | AIO, e.g., ES, pref. THF or diethyl ether | Yes |
| AB (Oxidation) | 1–3.5 moles, pref. 1.2–3 moles, pyridinium chlorochromate or pyridinium dichromate, 5–10 moles, pref. 6–8 moles, chromium trioxide (pref. complexed with pyridine, more pref. 2 moles pyridine per mole chromium trioxide), 5–50 moles, pref. 10–20 moles, manganese dioxide, pref. activated manganese dioxide, or, pref., 2–4 moles N—methylmorpholine-N—oxide monohydrate and and catalytic amount (e.g., 0.02–0.05 mole) tris(triphenylphosphine)ruthenium (II) chloride (CXI), per mole XLII. | 20°–30° C., pref. 20°–25° C. | 2–18 hrs., pref. 3–12 hrs., with pyridinium chlorochromate or chromium trioxide, 8–24 hrs., pref. 15– 18 hrs., with pyridinium dichromate, 4–48 hrs., pref. 10–24 hrs., with | AIO, pref. HLA, esp. methylene chloride, for pyridinium chlorochromate, chromium trioxide or pyridinium dichromate pref. HLA or ES, esp. diethyl ether, for manganese dioxide and dry acetone for N—methylmorpholine-N—oxide | Yes |

-continued

| Reaction/Type | Reagents, Molar Ratios and Comments | Temperature | Time | Solvent | Inert Atmosphere |
|---|---|---|---|---|---|
| | | | manganese dioxide and 1–5 hrs. with N—methyl-morpholine-N—oxide monohydrate | monohydrate | |
| AC (Wittig) | (1) Synthesis of ylide: 1–1.05 moles strong base, e.g., sodium hydride, phenyllithium or, pref., n-butyllithium per mole XLIV. Pref., slowly add solution of strong base to solution of XLIV. | −40°–0° C., pref. −35°–−20° C. | 1–4 hrs. | AIO, pref. ES, e.g., THF | Yes |
| | (2) Synthesis of enol ether: Ylide from 1–1.05 moles XLIV per mole XLIII. | −30°–0° C., pref. −20°–0° C. | 1–4 hrs. | Same as Step 1 | Yes |
| AC (Wittig) (Cont'd) | (3) Hydrolysis of enol ether: Large molar excess, e.g., 2–20 moles, strong acid, e.g., 70% perchloric acid, per mole XLIII used in Step 2 | 0°–30° C. | 8–24 hrs. | Mixture of aqueous acid and ES, e.g., mixture of 70% perchloric acid and THF | — |
| AD (Wittig) | Same as Reaction AC (Molar quantities in Steps 2 and 3 are per mole XLV). | Same as AC | Same as AC | Same as AC | Same as AC |
| AE (Wittig) | Same as Reaction AC (Molar quantities in Steps 2 and 3 are per mole XLVI). | Same as AC | Same as AC | Same as AC | Same as AC |
| AF (Wittig) | Alternative a:<br>1–2 moles, pref. 1–1.7 moles, XLVIII per mole XLIII. | 80° C.-reflux, esp. refluxing toluene | 6–18 hrs. | AIO, pref. HC, esp. toluene | Yes |
| | Alternative b:<br>(1) Synthesis of ylide: 1–1.07 moles strong base, pref. sodium hydride, per mole XLIX. Pref., add small amount of XLIX to suspension of sodium hydride in THF stirred at 20°–25° C., cool to −20°– −15° C. once reaction commences and complete reaction at −20°– −15° C. | −20°–25° C., pref. −20°–0° C. | 0.75–2 hrs. | AIO, pref. ES, esp. THF | Yes |
| | (2) 1–1.6 moles ylide from XLIX (assuming 100% conversion of XLIX to ylide) per mole XLIII. Pref., add solution of XLIII to ylide solution at −20°– −15° C., stir at −20°–25° C. for balance of reaction and, if necessary, complete reaction at 40°–65° C. | −20°–65° C. | 0.75–20 hrs. | Same as Step 1 | Yes |
| AG (Reduction) | (1) At least 2 equivalents transferable hydride from a metal hydride reducing agent, e.g., lithium aluminum hydride or diisobutylaluminum hydride, per mole L, pref. 3.8–6 moles diisobutylaluminum hydride per mole L. | −78°–25° C., pref. −78°– −20° C. | 0.7–3 hrs. | AIO, pref. ES, e.g., THF | Yes |
| | (2) Quench with, for example, water or saturated ammonium chloride or sodium sulfate solution. | −78°–25° C. | 5–15 min. | — | — |
| AH (Oxidation) | 5–50 moles, pref. 10–30 moles, manganese dioxide, pref. activated manganese dioxide, or, pref., 2–4 moles N—methylmorpholine-N—oxide monohydrate and catalytic amount (e.g., 0.02–0.05 mole) CXI, per mole LI. | 20° C.-reflux pref. 20°–40° C. with manganese dioxide and 20°–25° C. with N—methyl-morpholine-N—oxide monohydrate | 3–24 hrs., pref. 10–18 hrs. | AIO, pref. HC or ES, esp. diethyl ether, with manganese dioxide and dry acetone with N—methyl-morpholine-N—oxide monohydrate | Yes with N—methyl-morpholine-N—oxide monohydrate |
| AI | (p) Preparation of LIII: 2–2.1 moles, pref. 2 moles, t-butyllithium, pref. as 1–2M. solution in pentane, per mole cis-1-bromo-2-ethoxyethylene. | −80°– −75° C., pref. −78° C. | 1–5 hrs., pref. 2–4 hrs. | AIO, e.g., ES, pref. THF | Yes |
| AI (Cont'd) | (1) 1–1.75 moles LIII (assuming 100% yield from Step p) per mole XLIII. When Pr is PrC wherein R₄ is hydrogen, utilize an extra equivalent of LIII, i.e., 2–2.75 moles LIII per mole XLIII. When it is desired to isolate and/or purify the crude enol ether intermediate, quench the reaction mixture with, e.g., saturated ammonium chloride solution at −80°– −25° C. for 1–5 min. Otherwise, quenching is optional since it will occur at the beginning of Step 2. Crude enol ether | −80°– −40° C., pref. −80°– −60° C. | 0.75–8 hrs. pref. 1–4 hrs. | Same as Step p | Yes |

| Reaction/Type | Reagents, Molar Ratios and Comments | Temperature | Time | Solvent | Inert Atmosphere |
|---|---|---|---|---|---|
| (Hydrolysis) | product of this step may be used in next step without isolation and purification but isolation and purification of enol ether intermediate may improve yield of LII from next step. (2) Catalytic amount of p-toluenesulfonic acid or monohydrate thereof (e.g., 0.5–100 g., pref. 1–5 g., per mole XLIII used in Step (1) and water. | 20°–40° C., pref. 20°–25° C. | 0.5–5 hrs., pref. 0.5–4 hrs. | Mixture of ES and water, pref. mixture of THF and water | — |
| BA (Halogenation) | 1–2 moles, pref. 1.5–1.8 moles, LV or LVI per mole XLII. | −10°– −80° C. | 2–18 hrs. | AIO, pref. ES, e.g., diethyl ether or THF, HLA, e.g., methylene chloride, or HC, e.g., benzene | — |
| BB | Excess triphenylphosphine, e.g., 2–10 moles per mole LVII. | 60° C.-reflux, pref. <150° C., esp. 75°–78° C. (in absolute ethanol) | 0.5–24 hrs. | AIO, pref. absolute ethanol | Yes |
| BC | 1–1.1 moles LIX per mole LVII. Can use excess LIX as the solvent. | 20°–140° C., usually 110°–140° C. | 6–24 hrs., usually 10–16 hrs. | HC, e.g., benzene or xylene or neat (excess LIX is solvent) | Yes |
| BD | Same as Reaction B, Alternative a (Molar quantities are per mole XLV). | Same as B, a | Same as B, a | Same as B, a | Yes |
| BE (Halogenation) | Same as Reaction BA (Molar quantities are per mole LXI). | Same as BA | Same as BA | Same as BA | — |
| BF | Same as Reaction BB (Molar quantities are per mole LXII). | Same as BB | Same as BB | Same as BB | Yes |
| BG | Same as Reaction BC (Molar quantities are per mole LXII). | Same as BC | Same as BC | Same as BC | Yes |
| CA (Halogenation) | 1 mole LXVII per mole LXVI. In this reaction, LXVII is pref. Br$_2$. | 0°–40° C. | 2–18 hrs. | AIO, pref. HLA, e.g. chloroform | — |
| CB | 1–2 moles triphenylphosphine per mole LXVIII | 20°–40° C., pref. 20°–25° C. | 8–24 hrs. | AIO, pref. ES or HC, esp. toluene | Yes |
| CC (Wittig) | (1) 1–1.02 moles base, e.g., sodium ethoxide, per mole LXIX. | 20°–80° C. | 0.25–4 hrs. | AIO, pref. lower alkanol, esp. ethanol | Yes |
| | (2) 1–1.25 moles LXX per mole LXIX used in Step 1. | 60°–80° C. | 8–24 hrs. | Same as Step 1 | Yes |
| CD | (1) 1–1.3 moles base, e.g., sodium hydroxide, per mole LXVI. | 20°–30° C. | 5–15 min. | Mixture of lower alkanol, pref. ethanol, and water | — |
| | (2) 1–1.05 moles LXX per mole LXVI. Add LXX at 0°–5° C. and allow to warm to 20°–25° C. | 0°–5° C. → 20°–25° C. | 2–5 hrs. | Same as Step 1 | — |
| CE | (1) 1–1.08 moles strong base, pref. lithium diisopropylamide, per mole LXXII. | −80°– −60° C., pref. −78° C. | 0.4–1 hr. | AIO, pref. ES, esp. THF | Yes |
| | (2) 1–1.03 moles carbanion of LXXII (assuming 100% conversion of LXXII to its carbanion) per mole LXXI. | Same as Step 1 | 2–5 hrs. | Same as Step 1 | Yes |
| | (3) Quench with, for example, saturated ammonium chloride solution. | Same as Step 1 | 1–5 min. | Same as Step 1 | — |
| CF | 5.5–6.5 moles, pref. 6 moles, N—bromosuccinimide per mole LXXIII. | 0° C. | 3–6 hrs. | Mixture of acetonitrile and water, pref. a 4:1 mixture | — |
| CG | 1–4 moles, pref. 2–4 moles, LXXV and 0.4–1 mole, pref. 0.6 mole, titanium tetrachloride per mole LXXIV. Pref., combine reactants at 0° C., allow to warm to 20°–25° C. and heat at 100°–120° C. for 10–22 hrs., e.g., reflux in toluene for 16 hrs. | 0°–120° C., pref. 0°→ 111° C. | 12–24 hrs. | AIO, pref. HC, esp. mixture of hexane and toluene | Yes |

In the preceding table,
AIO=anhydrous inert organic solvent
ES=ether solvent, for example, diethyl ether, 1,2-diethoxyethane, 1,2-dimethoxyethane, tetrahydrofuran and mixtures thereof
esp.=especially
HC=hydrocarbon solvent, for example, benzene, toluene, xylene and mixtures thereof
HLA=halogenated lower alkane solvent, for example, carbon tetrachloride, chloroform, 1,1- dichloroethane, 1,2-dichloroethane, methylene chloride and 1,1,2-trichloroethane, usually preferably methylene chloride hr. (hrs.) = hour(s)
IO = inert organic solvent
min. = minutes
pref. = preferably, preferred
THF = tetrahydrofuran Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvent and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an inert atmosphere is not specified, are carried out under an inert atmosphere, usually dry nitrogen, for convenience.

In the preceding table, n-butyllithium is preferably employed as a 1.3-1.7M. solution in hexane, and lithium diisopropylamide is preferably prepared in situ from n-butyllithium and diisopropylamine.

Reactions analogous to Reactions A-J, L-N, P-V, AA-AH, BA, BB, BD-BF and CB are described in detail in copending application Ser. No. 06/722,288, filed by Faizulla G. Kathawala on Apr. 11, 1985 and title Indole Analogs Of Mevalonolactone And Derivatives Thereof. These reactions may be carried out analogously to the corresponding reactions of said application. Said application is hereby incorporated by reference. Generally, where the reaction conditions set forth in said application differ from those set forth in this specification, the reaction conditions set forth in said application may also be utilized for the compounds of this specification.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

Some of the reactions described above may yield mixtures of two or more products only one of which leads to the desired compound of Formula I. Any obtained mixture may be separated by conventional techniques such as those set forth in the preceding paragraph.

As is evident to those in the art, each of the compounds of Formulae III, VIII, XI and XIV has a single center of asymmetry and, therefore, may be resolved into two optically active isomers. When a compound of Formula III, VIII or XIV is converted into a compound of Formula IV, IX or XVI, respectively, an additional center of asymmetry is generated. Consequently, when a racemic compound of Formula III, VIII or XIV is utilized, four stereoisomers (two pairs of diastereoisomers) of the resulting compound of Formula IV, IX or XVI are formed, whereas when an optically pure compound of Formula III, VIII or XIV is utilized, two diastereoisomers of the compound of Formula IV, IX or XVI are formed.

The compounds of Formulae I (including those of Formulae IB, IC, V, XVIII, XXIII, XXV, etc.), IV, XVI, XXI XXII and XXIV have two centers of asymmetry and, therefore, may exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) of four (if formed from a racemic compound having one center of asymmetry) stereoisomers.

The one or two centers of asymmetry of each compound of Formulae LXVIII, LXIX, LXXIII and LXXIV may be ignored since each center of asymmetry is destroyed in a following reaction (Reaction CG).

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XXXVI may, for example, be separated by HPLC into its cis and trans (lactone) components, each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and/or HPLC. For example, a racemic lactone of Formula XXXVI may be reacted with an excess of R-(+)-α-methylbenzylamine (or the corresponding S-(−) compound) to form a mixture of two diastereoisomeric α-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°-25° C. for 16-24 hours. The reaction is run neat, with the excess amine serving as the solvent. After the reaction, the excess amine is removed by vacuum distillation at 25°-35° C. After separation, each chiral amide may be hydrolyzed to the corresponding, for example, sodium, salt by, for example, refluxing with 1.5-3, preferably 2-2.2, equivalents of a base such as sodium hydroxide for 5-25 hours in a mixture of water and ethanol. The resulting salts may be converted to the corresponding free acids, ester, lactones and other salts by conventional means such as the reactions set forth in Reaction Scheme IV. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, e.g., (−)-α-naphthylphenylmethylchlorosilane (Sommer et. al., J. Am. Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula XXXVI may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, the process conditions disclosed for Reactions J, L, N and P may be utilized to cleave (−)-α-naphthylphenylmethylsilyl and other silyl groups.

The compounds of Formulae II, VII, X, XII, XIII, XV, XVII, XXXIV, XXXVII, XLIV, XLVIII, XLIX, LIII, LV, LVI, LIX, LXVI-LXXII, LXXV and LXXVI, and the reagents not designated by a Roman numeral are known or, if unkown, may be synthesized by processes analogous to those described in the literature for similar known compounds.

The compounds of Formula XLI are also either known or, if unknown, may be synthesized by processes analogous to those described in the literature for the known compounds of said formula and similar compounds. See, for example, Barton, Tetrahedron Letters 25, 3707-3710 (1984), McKinnon, Canadian J. Chem. 43, 2628-2631 (1965), Patterson, Synthesis 1976, 281-304 and Sundberg, *Comprehensive Heterocyclic Chemistry, The Structure, Reactions, Synthesis and Uses of Heterocyclic Compounds*, Vol. 4, Part 3, Bird et al. ed., Pergamon Press, Oxford (1984), pp. 313-374, and the references cited in each which are hereby incorporated by reference. A synthesis of the compounds of Formula XLI useful for the synthesis of the preferred compounds of Formula I is described in Reaction Scheme VII.

A preferred process for the synthesis of the erythro racemate of the compound of Formula XXI wherein $R_{17}$ is hydrogen, $R_{19}$ is methyl, and $X_3$ is a direct bond is disclosed in Kapa, Tetrahedron Letters 25, 2435-2438 (1984). The other compounds of Formula XXI wherein $R_{17}$ is hydrogen, and $X_3$ is a direct bond in racemic erythro form may be synthesized similarly. See also U.S. Pat. No. 4,571,428. Said patent, particularly columns 3-11 thereof, is hereby incorporated by reference.

The compounds of Formulae XXI and XXVI and their synthesis are disclosed in U.S. Pat. No. 4,613,610. Said patent, particularly columns 19-24, 27-30 and 41-48 thereof, is hereby incorporated by reference.

Since any compound of Formula I wherein Z is a group of Formula a wherein $R_{18}$ is a cation other than M may be converted into the corresponding compound wherein $R_{18}$ is hydrogen, M or $R_{19}$ by the processes of Reaction Scheme IV, the compounds of Formula I wherein Z is a group of Formula a and $R_{18}$ is a pharmaceutically unacceptable cation are also within the scope of this invention since they are useful as intermediates. However, such compounds are not compounds of Formula I as utilized in this, except where indicated to the contrary.

Also within the scope of this invention are the intermediates of Formulae III, IV, VIII, XI, XIV, XVI, XIX, XX, XXII, XXIV, XXVII, XXIX, XLV-XLVII and L-LII. The preferences for each variable are the same as those set forth for the compounds of Formula I, with the preferred groups of such compounds including those that correspond to Groups (xix)-(xxxvi) and (xlix)-(lx) (for Formulae XXVII and XXIX) and Groups (i)-(xviii) and (xxxvii)-(xlviii) (for each of the others) to the extent consistent therewith.

The entire specification of parent application Ser. No. 06/791,198, now abandoned, particularly pages 1-15, 23, 26, 41-44 and 51-53 thereof, is hereby incorporated by reference as if set forth herein in its entirety.

Besides having the utility set forth below, every compounf of Formula I is useful as an intermediate in the synthesis of one or more other compounds of Formula I utilizing the reactions set forth in Reaction Scheme IV.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following tests:

Test A. In Vitro Microsomal Assay of HMG-CoA Reductase Inhibition:

This test is carried out precisely as described in column 53 of U.S. Pat. No. 4,613,610 and on page 30 of World (PCT) Published Patent Application No. 84/02131, both of which are hereby incorporated by reference as if set forth herein in their entirety. The concentration of the test substance (compound of Formula I) in the assay system is 0.0005-2,000 μmolar. The obtained $IC_{50}$ is the concentration of the test substance in the assay system observed or calculated to produce a 50% inhibition of HMG-CoA reductase activity.

Test B. In Vivo Cholesterol Biosynthesis Inhibition Test:

This test is carried out precisely as described in column 53 of said U.S. Pat. No. 4,613,610 and on page 33 of World (PCT) Published Patent Application No. 84/02131, both of which are hereby incorporated by reference as if set forth herein in their entirety. In this test the rats are orally administered the test substance (compound of Formula I) at a dose of 0.1-200 mg/kg. body weight. The obtained $ED_{50}$ is the dose of the test substance observed or calculated to produce a 50% inhibition of 3β-hydroxysterol synthesis.

In Test A, tested compounds of Formula I had $IC_{50}$'s of 0.014-0.454 μmolar whereas that of Compactin was 1.1 μmolar and that of Mevinolin was 0.72 μmolar. The preferred compound of this application, that of Example 2, had an $IC_{50}$ of 0.014 μmolar. In Test B, tested compounds of Formula I had $ED_{50}$'s of 0.53-0.97 mg/kg. whereas that of Compactin was 3.5 mg./kg. and that of Mevinolin was 0.41 mg./kg. The $ED_{50}$ of the preferred compound, that of Example 2, was 0.53 mg./kg.

Since they inhibit cholesterol biosynthesis, the compounds of Formula I (including those of each subgroup thereof) are useful for lowering the blood cholesterol level in animals, e.g., mammals, especially larger primates, in particular humans, and, therefore, as hypolipoproteinemic and anti-atherosclerotic agents.

The precise dosage of the compound of Formula I to be employed for inhibiting cholesterol biosynthesis depends upon several factors including the host, the nature and the severity of the condition being treated, the mode of administration and the particular active substance (compound of Formula I) employed. However, in general, suitable oral daily dosages of the compounds of Formula I for the satisfactory inhibition or reduction of cholesterol biosynthesis (i.e., the satisfactory reduction of blood cholesterol level and satisfactory treatment of hyperlipoproteinemia and atherosclerosis) are indicated by the test data to be 0.06-100 mg./kg. body weight, e.g., 0.06-6 mg./kg. body weight for the more active compounds. For most larger primates such as humans, a suitable oral daily dosage is indicated to be 4-2,000 mg., e.g., 4-200 mg. for the more active compounds. The daily dosage of the compound of Example 2 is indicated to be 4-200 mg., preferably 10-40 mg., for most larger primates such as humans. For administration by injection, a dosage somewhat lower than would be used for oral administration of the same active substance to the same host having the same condition is usually employed. However, the above dosages are also typically used for i.v. administration.

The daily dosage may be administered in a single dose but more typically is administered in two to four equal portions, typical doses being 1-2,000 mg. Often, a small dosage is administered initially, and the dosage is gradually increased until the optimal dosage for the host under treatment is determined.

A typical dosage unit for oral administration may contain 1-500 mg. of a compound of Formula I.

The compounds of Formula I may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I and at least one pharmaceutically acceptable solid or liquid carrier (or diluent). They may be formulated in conventional manner. The compounds of each subgroup thereof may likewise be formulated into such pharmaceutical compositions and administered by such routes.

The compounds of Formula I (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

A representative formulation suitable for encapsulation in a hard gelatin capsule by conventional techniques is:

Compound of formula I, e.g., the compound of

| | |
|---|---|
| Example 2 | 5 mg. |
| Corn starch | 244 mg. |
| Magnesium stearate | 1 mg. |

The following examples show representative compounds encompassed by this invention and their synthesis. However, it should be understood that they are for purposes of illustration only.

EXAMPLE 1

Ethyl (±)-erythro-(E)-3,5-dihydroxy-7-[1'-(4''-fluorophenyl)-3'-(1'''-methylethyl)-5'-phenyl-1H-pyrrol-2'-yl]hept-6-enoate

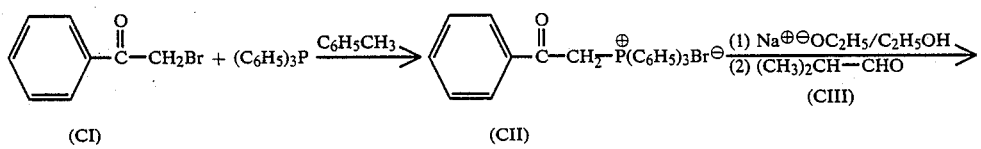

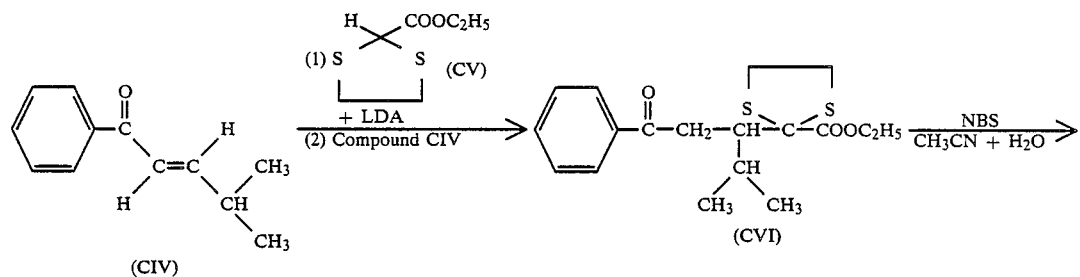
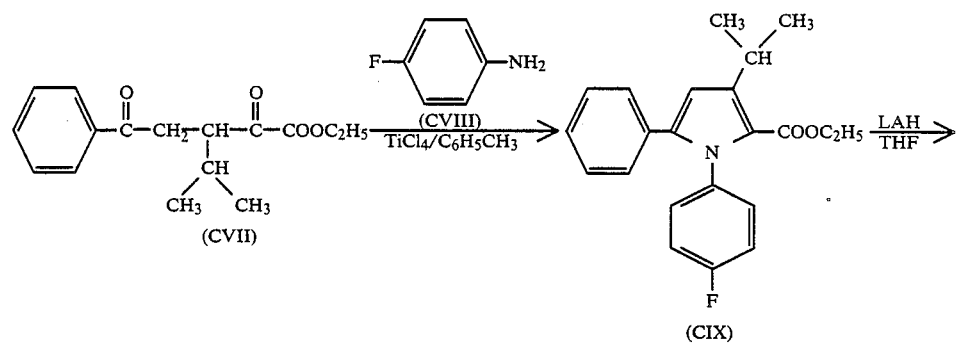
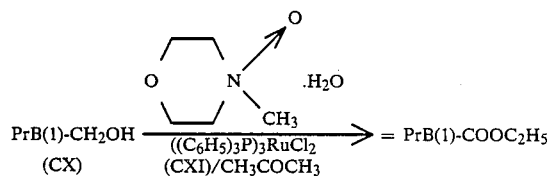
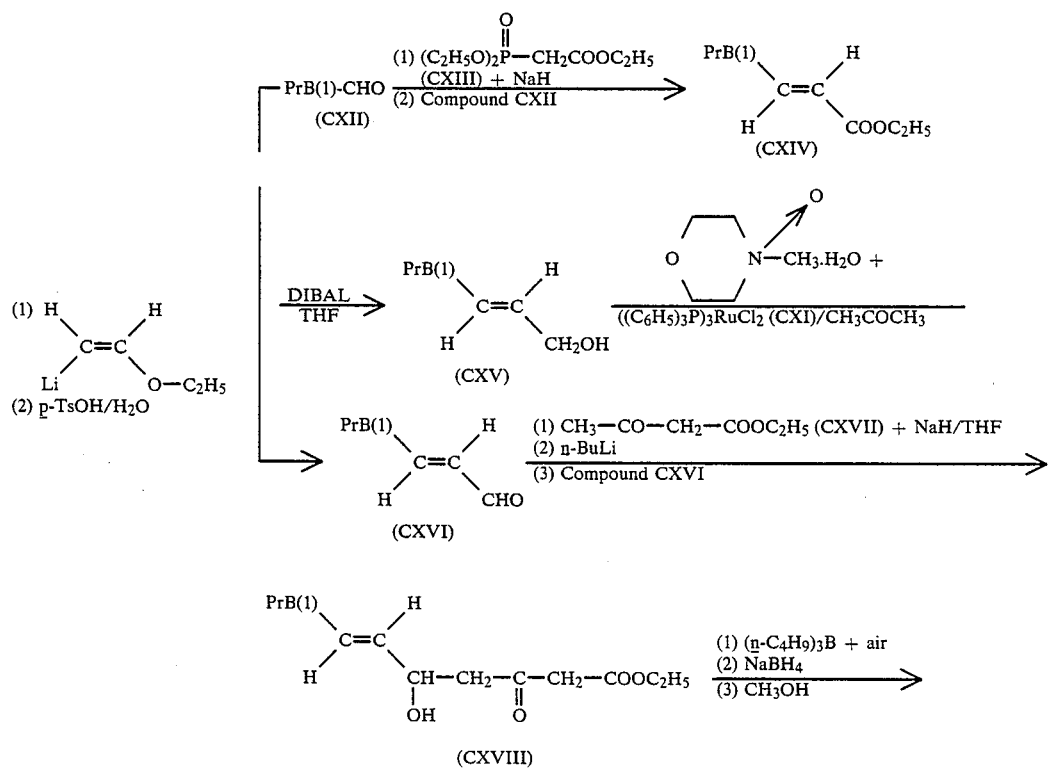

-continued

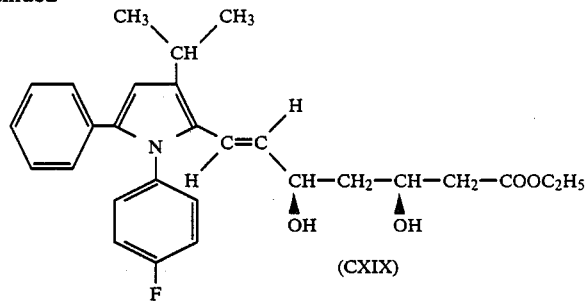

(CXIX)

Step 1 (Reaction CB)

(2-Oxo-2-phenylethyl)triphenylphosphonium bromide (Compound CII)

50.0 g. (251 mmoles) of α-bromoacetophenone (Compound CI) and 65.9 g. (251 mmoles) of triphenylphosphine are stirred in 500 ml. of toluene at 20°-25° C. under nitrogen for 16 hours, and the resulting solid is collected by filtration, rinsed with toluene and rinsed with diethyl ether to obtain the product as a white powder (107.98 g. (93%)).

Step 2 (Reaction CC)

(E)-4-Methyl-1-phenylpent-2-en-1-one (Compound CIV)

A solution of 6.64 g. (289 mmoles) of sodium in 250 ml. of absolute ethanol is quickly added dropwise to a suspension of 133.3 g. (289 mmoles) of Compound CII in 1 l. of absolute ethanol stirred at 20°-25° C., the suspension is gently warmed until a clear solution results, 31.5 ml. (25.0 g.; 347 mmoles) of isobutyraldehyde is added dropwise to the solution, and the reaction mixture is refluxed for 16 hours and cooled to 20°-25° C., the reaction mixture being maintained under dry nitrogen throughout. The reaction mixture is evaporated at reduced pressure, the resulting oily solid is triturated with diethyl ether, and the insoluble material is removed by filtration. The diethyl ether solution is washed with water, washed twice with saturated sodium chloride solution, dried over anhydrous magnesium sulfate, filtered and evaporated at reduced pressure. The residue is triturated with diethyl ether, any insoluble material is removed by filtration, and the diethyl ether is evaporated at reduced pressure to obtain a clear yellow liquid which is fractionally vacuum distilled through a vacuum jacketed Vigreux column to obtain the product as a clear liquid (22.8 g.), b.p. 90°-92° C./~1 mm. Hg.

Step 3 (Reaction CE)

Ethyl (±)-2-[1'-(1''-methylethyl)-2'-oxo-2'-phenylethyl]-1,3-dithiolane-2-carboxylate (Compound CVI)

83 ml. of 1.65M. n-butyllithium/hexane (138 mmoles) is added via syringe to a solution of 20.2 ml. (14.58 g.; 144 mmoles) of diisopropylamine in 200 ml. of dry tetrahydrofuran (distilled from ketyl) stirred at −78° C., the reaction mixture is warmed to 0° C. and cooled to −78° C., 18.7 ml. (23.35 g.; 131 mmoles) of ethyl 1,3-dithiolane-2-carboxylate (Compound CV) is added dropwise to the reaction mixture stirred at −78° C., the reaction mixture is stirred at −78° C. for 30 minutes, a solution of 22.749 g. (131 mmoles) of Compound CIV in 50 ml. of dry tetrahydrofuran (distilled from ketyl) is added dropwise with stirring at −78° C., and the reaction mixture is stirred at −78° C. for 3 hours, the reaction mixture being maintained under dry nitrogen throughout. The reaction mixture is quenched at −78° C. with saturated ammonium chloride solution and warmed to 20°-25° C., the tetrahydrofuran is evaporated at reduced pressure, and the residue is partitioned between ethyl acetate and water. The aqueous phase is acidified to about pH 2 with 10% hydrochloric acid and extracted with ethyl acetate. The ethyl acetate layers are combined, washed twice with saturated sodium chloride solution, dried over anhydrous magnesium sulfate, filtered and evaporated at reduced pressure. The residue is triturated with diethyl ether to obtain the crude product as a white solid (27.13 g.).

Step 4 (Reaction CF)

Ethyl (±)-2,5-dioxo-3-(1'-methylethyl)-5-phenylpentanoate (Compound CVII)

A solution of 27.1 g. (76.9 mmoles) of crude Compound CVI from Step 3 in 200 ml. of acetonitrile is added dropwise to a solution of 82.1 g. (461.3 mmoles) of N-bromosuccinimide in 500 ml. of a 4:1 mixture of acetonitrile and water stirred at 0° C., the reaction mixture is stirred at 0° C. for 4.5 hours, sufficient saturated sodium carbonate solution is added to obtain a clear solution, the acetonitrile is evaporated at reduced pressure, the residue is partitioned between ethyl acetate and water, the aqueous phase is acidified to about pH 2 with 10% aqueous hydrochloric acid and extracted with ethyl acetate, and the ethyl acetate layers are combined, washed twice with saturated sodium chloride solution, dried over anhydrous magnesium sulfate, filtered and evaporated at reduced pressure to obtain the crude product as a clear yellow liquid (23.49 g.).

Step 5 (Reaction CG)

Ethyl 1-(4'-fluorophenyl)-3-(1'-methylethyl)-5-phenyl-1H-pyrrole-2-carboxylate (Compound CIX)

24.59 g. (89 mmoles) of crude Compound CVII from Step 4 and 16.9 ml. (19.8 g.; 178 mmoles) of 4-fluoroaniline are stirred at 0° C. in 350 ml. of toluene, a solution of 5.9 ml. (10.13 g.; 53.4 mmoles) of titanium tetrachloride in 50 ml. of hexane is added dropwise with stirring at 0° C., and the reaction mixture is allowed to slowly warm to 20°-25° C. and refluxed for 16 hours, the reaction mixture being maintained under dry nitrogen throughout. The reaction mixture is filtered through a pad of Celite, the Celite is rinsed with ethyl acetate, and the rinse and filtrate are combined and evaporated at reduced pressure to obtain a brown solid (25.1 g.). The brown solid is recrystallized from absolute ethanol to obtain slightly colored needles (16.74 g.), a second crop is obtained from the absolute ethanol (2.87 g.), and the two crops are combined and recrystallized from absolute ethanol to obtain the product as a white powder (15.49 g.).

A small sample is dissolved in the minimum amount of methylene chloride and flash chromatographed on 250 g. of 230–400 mesh A.S.T.M. silica gel utilizing 25% diethyl ether/hexane as the eluant, the eluant is evaporated, and the residue is recrystallized from absolute ethanol to obtain an analytical sample, m.p. 107°–110° C.

Step 6 (Reaction AA)

1-(4'-Fluorophenyl)-3-(1'-methylethyl)-5-phenyl-1H-pyrrole-2-methanol (Compound CX)

A solution of 15.0 g. (42.7 mmoles) of Compound CIX in 100 ml. of dry tetrahydrofuran (distilled from ketyl) is added dropwise to a suspension of 4.86 g. (128.1 mmoles) of lithium aluminum hydride in 150 ml. of dry tetrahydrofuran (distilled from ketyl) stirred at 0° C., and the reaction mixture is allowed to warm to 20°–25° C., stirred at 20°–25° C. for 3 hours and cooled to 0° C., the reaction mixture being stirred under dry nitrogen throughout. The reaction mixture is quenched at 0° C. with water, the white gum is removed by filtration, the small aqueous phase is separated and the organic phase is washed twice with saturated sodium chloride solution, dried over anhydrous magnesium sulfate, filtered and evaporated at reduced pressure to obtain a white solid (12.59 g.) which is recrystallized from diethyl ether/hexane to obtain the product as a white powder (6.58 g.). The mother liquor is evaporated at reduced pressure, and the residue is recrystallized from methylene chloride/hexane to obtain a second crop (1.903 g.). Total yield: 8.48 g. (64%).

Revised procedure:

A solution of 29.6 g. (84.2 mmoles) of Compound CIX in 250 ml. of dry diethyl ether is added dropwise to a suspension of 9.6 g. (252.6 mmoles) of lithium aluminum hydride in 250 ml. of dry diethyl ether stirred at 0° C. under dry nitrogen, and the reaction mixture is stirred at 0° C. under dry nitrogen for 2 hours. The reaction mixture is quenched at 0° C. with water and filtered. The filtrate is washed with saturated sodium chloride solution, dried over anhydrous magnesium sulfate, filtered and evaporated at reduced pressure to obtain the crude product as a white solid (23.92 g. (92%)).

Step 7 (Reaction AB)

1-(4'-Fluorophenyl)-3-(1'-methylethyl)-5-phenyl-1H-pyrrole-2-carboxaldehyde (Compound CXII)

A solution of 7.8 g. (25.2 mmoles) of Compound CX in 200 ml. of dry acetone (dried over 4Å. molecular sieves) is added dropwise to a mixture of 483 mg. (0.5 mmole) of tris(triphenylphosphine)ruthenium(II) chloride (Compound CXI) and 8.62 g. (50.4 mmoles) of N-methylmorpholine-N-oxide.monohydrate in 100 ml. of dry acetone (dried over 4Å. molecular sieves) stirred at 20°–25° C., and the reaction mixture is stirred at 20°–25° C. for 4 hours, the reaction mixture being maintained under dry nitrogen throughout. The reaction mixture is filtered through 230–400 mesh A.S.T.M. silica gel, the silica gel is rinsed with diethyl ether, and the rinse and filtrate are combined and evaporated at reduced pressure to obtain a tan solid. The tan solid is dissolved in the minimum amount of methylene chloride and flash chromatographed on 450 g. of 230–400 mesh A.S.T.M. silica gel utilizing 25% diethyl ether/hexane as the eluant, and the eluant is evaporated at reduced pressure to obtain the product as a flocculant white solid (5.3 g. (68%)), m.p. 135°–139° C.

Revised procedure:

A solution of 24 g. (77.6 mmoles) of crude Compound CX (Step 6, revised procedure) in 250 ml. of dry acetone is added dropwise to a mixture of 1.5 g. (1.6 mmoles) of Compound CXI and 18 g. (154 mmoles) of N-Methylmorpholine-N-oxide.monohydrate in 250 ml. of dry acetone stirred at 20°–25° C., and the reaction mixture is stirred at 20°–25° C. for 4 hours, the reaction mixture being maintained under dry nitrogen throughout. 250 g. of 230–400 mesh A.S.T.M. silica gel is added, and the slurry is filtered through a 2 l. sintered glass funnel about one half full of the same silica gel. The silica gel is washed with 2 l. of 25% diethyl ether/hexane, and the filtrate and washing are combined and evaporated at reduced pressure. The obtained flocculant yellow solid is recrystallized from diethyl ether to obtain the product (13.12 g.). Additional product may be obtained from the mother liquor.

Step 8 (Reaction AF)

Ethyl (E)-3-[1'-(4''-fluorophenyl)-3'-(1'''-methylethyl)-5'-phenyl-1H-pyrrol-2'-yl]prop-2-enoate (Compound CXIV)

1.03 g. of 60% sodium hydride/mineral oil (25.7 mmoles) is washed twice with hexane and suspended in 100 ml. of dry tetrahydrofuran (distilled from ketyl), the suspension is stirred at 20°–25° C., approximately 1 ml. of triethyl phosphonoacetate (Compound CXIII) is added to initiate the reaction, the reaction mixture is cooled to −20°−−15° C., approximately 3.9 ml of triethyl phosphonoacetate is added dropwise with stirring at −20°−−15° C. (the total amount of triethyl phosphonoacetate being 4.9 ml. (5.48 g.; 24.45 mmoles)), the reaction mixture is stirred at −20°−−15° C. for 1 hour, a solution of 5.0 g. (16.3 mmoles) of Compound CXII in 50 ml. of dry tetrahydrofuran (distilled from ketyl) is added dropwise with stirring at −20°−−15° C., and the reaction mixture is allowed to warm to 20°–25° C., refluxed for 3 hours and stirred at 20°–25° C. for 16 hours, the reaction mixture being maintained under dry nitrogen throughout. The reaction mixture is diluted with diethyl ether and extracted with water, and the aqueous phase is reextracted with diethyl ether. The organic phases are combined, washed twice with saturated sodium chloride solution, dried over anhydrous magnesium sulfate, filtered and evaporated at reduced pressure to obtain a white solid which is recrystallized from diethyl ether to obtain the product as a white powder (4.877 g.). A second crop is obtained from diethyl ether/hexane (0.66 g.). Total yield: 5.54 g. (90%).

An analytical sample is obtained by recrystallization of a small sample from diethyl ether/hexane, m.p. 145°–147.5° C.

Step 9 (Reaction AG)

(E)-3-[1'-(4''-Fluorophenyl)-3'-(1'''-methylethyl)-5'-phenyl-1H-pyrrol-2'-yl]prop-2-en-1-ol (Compound CXV)

44 ml. of 1.5M. diisobutylaluminum hydride/toluene (66 mmoles) is added dropwise to a solution of 5.0 g.

(13.25 mmoles) of Compound CXIV in 100 ml. of dry tetrahydrofuran (distilled from ketyl) stirred at −78° C., and the reaction mixture is stirred at −78° C. for 1 hour, the reaction mixture being stirred under dry nitrogen throughout. The reaction mixture is quenched at −78° C. with water and warmed to 20°–25° C., sufficient 10% hydrochloric acid is added to dissolve the gel, and the mixture is extracted twice with diethyl ether. The diethyl ether extracts are combined, washed with saturated sodium bicarbonate solution, washed twice with saturated sodium chloride solution, dried over anhydrous magnesium sulfate, filtered and evaporated at reduced pressure. The residue is recrystallized from diethyl ether to obtain the product as a white powder (3.1 g.), m.p. 142°–148° C. The mother liquor is evaporated at reduced pressure, the residue is dissolved in the minimum amount of methylene chloride and flash chromatographed on 150 g. of 230–400 mesh A.S.T.M. silica gel utilizing 50% diethyl ether/hexane as the eluant, and the eluant is evaporated at reduced pressure to obtain additional product as a tan powder (0.53 g.). Total yield: 3.63 g. (82%).

Step 10 (Reaction AH)

(E)-3-[1'-(4''-Fluorophenyl)-3'-(1''-methylethyl)-5'-phenyl-1H-pyrrol-2'-yl]prop-2-en-1-al (Compound CXVI)

A solution of 3.3 g. (9.84 mmoles) of Compound CXV in 150 ml. of dry acetone (dried over 4Å. molecular sieves) is added dropwise to a mixture of 283 mg. (0.3 mmole) of tris(triphenylphosphine)ruthenium(II) chloride (Compound CXI) and 2.31 g. (19.68 mmoles) of N-methylmorpholine-N-oxide.monohydrate in 100 ml. of dry acetone (dried over 4Å. molecular sieves) stirred at 20°–25° C., the reaction mixture is stirred at 20°–25° C. for 3 hours, an additional 1.15 g. (9.84 mmoles) of N-methylmorpholine-N-oxide.monohydrate is added, the reaction mixture is stirred at 20°–25° C. for 2 hours, an additional 189 mg. (0.2 mmole) of tris(triphenylphosphine)ruthenium(II) chloride is added, and the reaction mixture is stirred at 20°–25° C. for 16 hours, the reaction mixture being stirred under dry nitrogen throughout. The reaction mixture is filtered through a pad of Celite and evaporated at reduced pressure to obtain a dark green oily solid which is dissolved in the minimum amount of methylene chloride and flash chromatographed on 250 g. of 230–400 mesh A.S.T.M. silica gel utilizing 25% diethyl ether/hexane as the eluant. The eluant is evaporated at reduced pressure to obtain the product as a yellow solid (2.49 g. (76%)), m.p. 180°–184° C.

Step 8A (Reaction AI)

(E)-3-[1'-(4''-Fluorophenyl)-3'-(1''-methylethyl)-5'-phenyl-1H-pyrrol-2'-yl]prop-2-en-1-al (Compound CXVI)

29 ml. of 1.7M. t-butyllithium/pentane (49.3 mmoles) is added dropwise to a solution of 2.6 ml. (3.72 g.; 24.6 mmoles) of cis-1-bromo-2-ethoxyethylene in 50 ml. of dry tetrahydrofuran stirred at −78° C., the reaction mixture is stirred at −78° C. for 4 hours, a solution of 5.0 g. (16.3 mmoles) of Compound CXII in 25 ml. of dry tetrahydrofuran is added dropwise with stirring at −78° C., and the reaction mixture is stirred at −78° C. for 45 minutes, the reaction mixture being maintained under dry nitrogen throughout. The reaction mixture is quenched with saturated ammonium chloride solution and warmed to 20°–25° C., the tetrahydrofuran is evaporated at reduced pressure, and the residue is partitioned between diethyl ether and water. The aqueous phase is extracted with diethyl ether, and the two diethyl ether phases are combined, washed twice with saturated sodium chloride solution, dried over anhydrous magnesium sulfate, filtered and evaporated to an orange gum at reduced pressure. The orange gum is dissolved in 100 ml. of a 9:1 mixture of tetrahydrofuran and water, 0.31 g. (1.63 mmoles) of p-toluenesulfonic acid.monohydrate is added, the reaction mixture is stirred at 20°–25° C. for 4 hours, the tetrahydrofuran is evaporated at reduced pressure, and the residue is partitioned between chloroform and water. The aqueous phase is extracted with chloroform, and the chloroform phases are combined, washed with saturated sodium chloride solution, dried over anhydrous magnesium sulfate, filtered and evaporated at reduced pressure to obtain a green solid. The green solid is dissolved in the minimum amount of chloroform, adsorbed onto 25 g. of 230–400 mesh A.S.T.M. silica gel and flash chromatographed on 400 g. of the same silica gel utilizing 1:1 diethyl ether/hexane as the eluant. The eluant is evaporated at reduced pressure to obtain the crude product as an orange solid (4.28 g. (79%)).

Step 11 (Reaction A)

Ethyl (±)-(E)-7-[1'-(4''-fluorophenyl)-3'-(1''-methylethyl)-5'-phenyl-1H-pyrrol-2'-yl]-5-hydroxy-3-oxohept-6-enoate (Compound CXVIII)

528 mg. (13.2 mmoles) of 60% sodium hydride/mineral oil is washed twice with hexane, the sodium hydride is suspended in 50 ml. of dry tetrahydrofuran (distilled from ketyl), the suspension is cooled to −20°−−15° C., 1.53 ml. (1.56 g.; 12.0 mmoles) of ethyl acetoacetate is added dropwise, the reaction mixture is stirred at −20°−−15° C. for 30 minutes, 7.6 ml. of 1.65M. n-butyllithium/hexane (12.54 mmoles) is added dropwise with stirring at −20°−−15° C., the reaction mixture is stirred at −20°−−15° C. for 15 minutes, a solution of 2.0 g. (6.0 mmoles) of Compound CXVI in 50 ml. of dry tetrahydrofuran (distilled from ketyl) is added dropwise with stirring at −15° C., and the reaction mixture is stirred at −15° C. for 2.5 hours, the reaction mixture being stirred under dry argon throughout. The reaction mixture is quenched at −15° C. with saturated ammonium chloride solution and warmed to 20°–25° C., the tetrahydrofuran is evaporated at reduced pressure, the residue is partitioned between diethyl ether and water, the aqueous phase is extracted with diethyl ether, and the diethyl ether phases are combined, washed twice with saturated sodium chloride solution, dried over magnesium sulfate, filtered and evaporated at reduced pressure to a brown oil. The brown oil is dissolved in the minimum amount of methylene chloride and flash chromatographed on 250 g. of 230–400 mesh A.S.T.M. silica gel utilizing 1:1 diethyl ether/hexane as the eluant, and the eluant is evaporated at reduced pressure to obtain the product as a yellow solid (2.51 g. (90%)).

A small sample is recrystallized from diethyl ether/hexane to obtain an analytical sample, m.p. 98°–101° C.

Revised procedure:

1.16 g. of 60% sodium hydride/mineral oil (29 mmoles) is washed with hexane, the sodium hydride is suspended in 100 ml. of dry tetrahydrofuran, the suspension is cooled to −20°–15° C., 3.3 ml. (3.37 g.; 25.9 mmoles) of ethyl acetoacetate is added dropwise, the reaction mixture is stirred at −20°—−15° C. for 30 minutes, 17 ml. of 1.6M. n-butyllithium/hexane (27.2 mmoles) is added dropwise with stirring at −20°—−15° C., the reaction mixture is stirred at −20°—−15° C. for 15 minutes, a solution of 4.28 g. (12.8 mmoles) of crude Compound CXVI (from Step 8A) in 100 ml. of dry tetrahydrofuran is added dropwise with stirring at −20°—−15° C. and the reaction mixture is stirred at −20°—−15° C. for 30 minutes, the reaction mixture being stirred under dry nitrogen throughout. The reaction mixture is quenched with saturated ammonium chloride solution and warmed to 20°-25° C., the tetrahydrofuran is evaporated at reduced pressure, and the residue is partitioned between diethyl ether and water. The aqueous phase is extracted with diethyl ether, and the diethyl ether phases are combined, washed twice with saturated sodium chloride solution, dried over anhydrous magnesium sulfate, filtered and evaporated at reduced pressure to obtain a dark orange oil. The dark orange oil is dissolved in the minimum amount of methylene chloride and flash chromatographed on 500 g. of 230-400 mesh A.S.T.M. silica gel utilizing 1:1 diethyl ether/hexane as the eluant. The fractions containing relatively pure product (as determined by thin layer chromatography) are combined and evaporated at reduced pressure to obtain the product as an oily solid (2.33 g.). The other fractions containing the product are combined, evaporated at reduced pressure, dissolved in the minimum amount of methylene chloride and flash chromatographed on 350 g. of 230-400 mesh A.S.T.M. silica gel utilizing, successively, 40%, 50% and 80% diethyl ether/hexane as the eluants. The fractions containing the product are combined and evaporated at reduced pressure to obtain additional product as an orange oil that solidifies upon standing (2.54 g.). Total yield: 4.87 g. (80.5%).

The product is a racemate which may be resolved to obtain the 5R and 5S enantiomers.

Step 12 (Reaction B)

Ethyl (±)-erythro-(E)-3,5-dihydroxy-7-[1'-(4''-fluorophenyl)-3'-(1''-methylethyl)-5'-phenyl-1H-pyrrol-2'-yl]hept-6-enoate (Compound CXIX)

(a) 4.32 ml. of 1.0M tri-n-butylborane/tetrahydrofuran (4.32 mmoles) is added quickly dropwise to a solution of 1.0 g. (2.16 mmoles) of Compound CXVIII in 25 ml. of dry tetrahydrofuran (distilled from ketyl) stirred at 20°-25° C., air is bubbled through the solution for 1 minute, the solution is stirred at 20°-25° C. for 1 hour and cooled to −78° C., 408 mg. (10.8 mmoles) of sodium borohydride is added with stirring at −78° C., and the reaction mixture is stirred at −50° C. for 16 hours and allowed to slowly warm to −20° C. to complete the reaction, the reaction mixture being stirred under dry nitrogen throughout. The reaction mixture is quenched at −20° C. with 10% hydrochloric acid (to pH 2), allowed to warm to 20°-25° C. and partitioned between diethyl ether and water. The aqueous phase is extracted with diethyl ether, and the organic phases are combined, washed twice with saturated sodium chloride solution, dried over anhydrous magnesium sulfate, filtered and evaporated at reduced pressure to a clear yellow oil. A small amount of isopropanol is added, and the isopropanol is evaporated at reduced pressure to obtain a yellow solid.

(b) The cyclic boron ester product of Part (a) is dissolved in methanol with heating and the methanol is evaporated at reduced pressure, and this procedure is repeated twice more to obtain a white solid which is recrystallized from methylene chloride/hexane to obtain the product as a flocculant white solid (295.2 g. (29%)), m.p. 140°-142° C.

Revised procedure:

(a) 10.0 ml. of 1.0M. tri-n-butylborane/tetrahydrofuran (10.0 mmoles) is added quickly dropwise to a solution of 2.33 g. (5.0 mmoles) of Compound CXVIII (Step 11, revised procedure, first fraction) in 100 ml. of 4:1 dry tetrahydrofuran/methanol stirred at 20°-25° C., air is bubbled in for 1 minute, the reaction mixture is stirred at 20°-25° C. for 1 hour and cooled to −78° C., 567 mg. (15.0 mmoles) of sodium borohydride is added, and the reaction mixture is stirred at −78° C. for 2 hours, the reaction mixture being maintained under dry nitrogen throughout. The reaction mixture is quenched at −78° C. with 4 ml. of acetic acid and warmed to 20°-25° C., the solvent is evaporated at reduced pressure, and the residue is partitioned between diethyl ether and water. The aqueous phase is extracted with diethyl ether, and the diethyl ether phases are combined, washed with saturated sodium chloride solution, dried over anhydrous magnesium sulfate, filtered and evaporated at reduced pressure to obtain a yellow solid (3.31 g.).

(b) The cyclic boron ester product of Part (a) is dissolved in methanol with heating and the methanol is evaporated at reduced pressure, and this procedure is repeated twice more to obtain an oily yellow solid which is recrystallized from methylene chloride/hexane to obtain the product as a white powder, m.p. 144.5°-146.5° C.

The product is a mixture of the erythro and threo racemates wherein the ratio of the former to the latter exceeds 9:1 (initial batch (m.p. 140°-142° C.)) or 19:1 (revised procedure batch (m.p. 144.5°-146.5° C.)), which mixtures may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a non-stereoselective reduction would afford a mixture of all four stereoisomers wherein the ratio of the erythro stereoisomers to the threo stereoisomers ranges from 3:2 to 2:3.

EXAMPLE 2

Sodium (±)-erythro-(E)-3,5-dihydroxy-7-[1'-(4''-fluorophenyl)-3'-(1''-methylethyl)-5'-phenyl-1H-pyrrol-2'-yl]hept-6-enoate

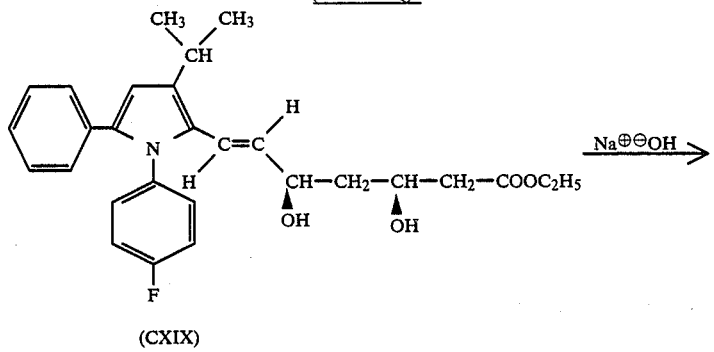

(CXIX)

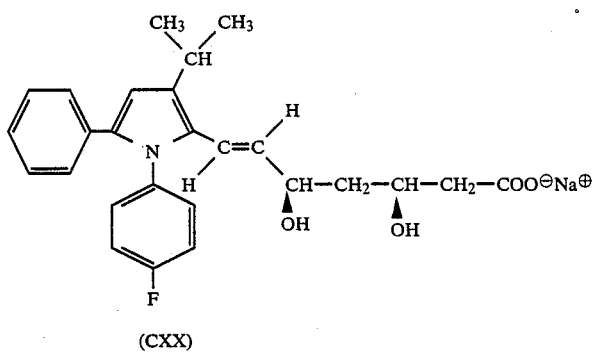

(CXX)

0.1 ml. of 0.5N. sodium hydroxide solution (0.05 mmole) is quickly added dropwise to a suspension of 25 mg. (0.054 mmole) of Compound CXIX in 5 ml. of absolute ethanol, and the reaction mixture is stirred at 20°–25° C. for 2 hours, diethyl ether is added, and the pale yellow precipitated product is collected, stirred in diethyl ether and collected by filtration (18 mg. (77%)), m.p. 175°–185° C. (dec.) (yellows at 145° C.).

N.M.R. (CD$_3$OD+CDCl$_3$): 1.21 (m, 6H), 1.60 (m, 2H), 2.29 (m, 2H), 3.12 (m, 1H), 3.95 (m, 1H), 4.20 (m, 1H), 5.40 (dd (J$_1$=15 Hz., J$_2$=7.5 Hz.), 1H), 6.22 (dd (J=15 Hz.), 1H), 6.30 (s, 1H), 7.08 (m, 9H)

Revised procedure:

19 ml. of 0.5N. sodium hydroxide solution (9.5 mmoles) is added dropwise to a suspension of 4.67 g. (10.0 mmoles) of Compound CXIX (Example 1, Step 12, revised procedure) in about 200 ml. of absolute ethanol stirred at 20°–25° C., and the reaction mixture is stirred at 20°–25° C. for 3 hours. The reaction mixture is concentrated at reduced pressure by about one third, and diethyl ether is added to obtain a pale yellow powder (3.7 g.). The powder is stirred in diethyl ether at 20°–25° C. for 30 minutes, and the fine pale yellow product is collected by filtration. M.p. 203°–206° C. (dec.) Additional product is obtained from the mother liquors. The combined yield of this batch and a similar smaller one is about 81%.

The product is a mixture of the erythro and threo racemates wherein the ratio of the former to the latter exceeds 9:1 (initial batch (m.p. 175°–185° C. (dec.))) or 19:1 (revised procedure batch (m.p. 203°–206° C. (dec.))), which mixtures may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a starting material synthesized by using a non-stereoselective reduction in Step 12 of Example 1 would afford a mixture of all four stereoisomers wherein the ratio of the erythro stereoisomers to the threo stereoisomers ranges from 3:2 to 2:3.

EXAMPLE 3

Ethyl (E)-3,5-dihydroxy-7-[3'-(4''-fluorophenyl)-1'-(1''-methylethyl)-5'-phenyl-1H-pyrrol-2'-yl]hept-6-enoate

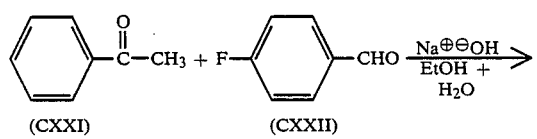

(CXXI)    (CXXII)

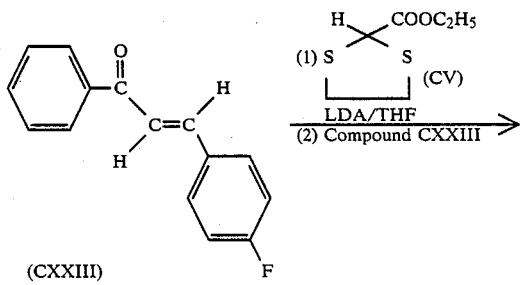

(CXXIII)

-continued

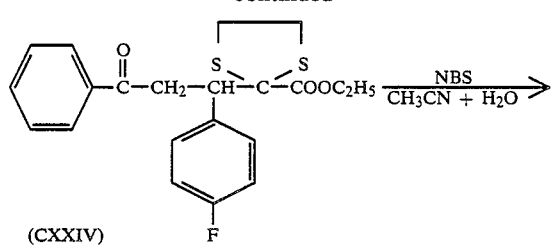

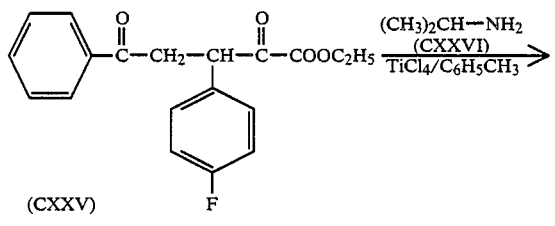

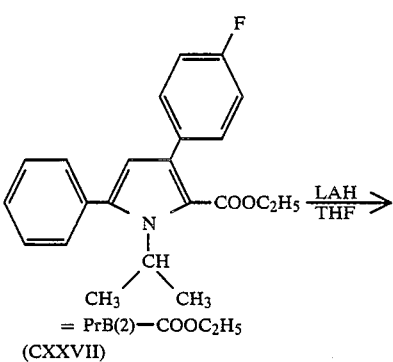

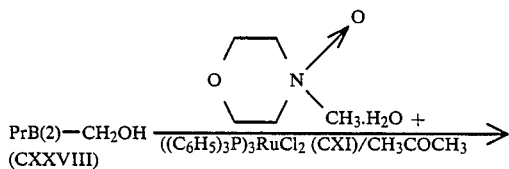

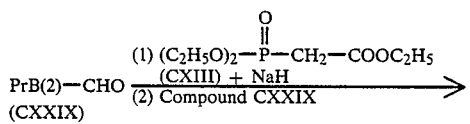

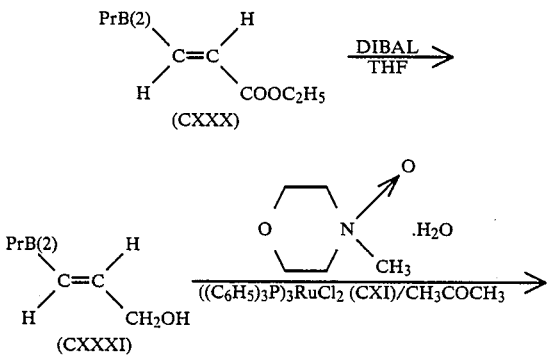

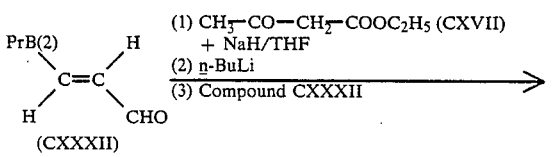

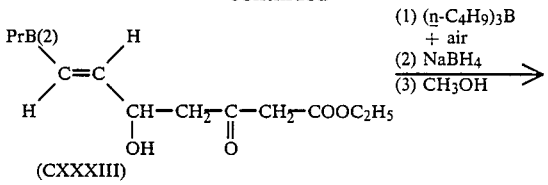

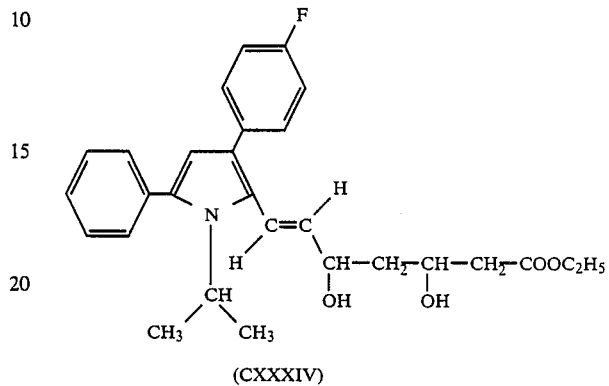

Step 1 (Reaction CD)

(E)-3-(4'-Fluorophenyl)-1-phenylprop-2-en-1-one (Compound CXXIII)

52.0 g. (433 mmoles) of acetophenone is added to a solution of 21.8 g. (545 mmoles) of sodium hydroxide in a mixture of 196 ml. of water and 122.5 ml. of 95% ethanol stirred at 20°-25° C., the resulting suspension is cooled to 0°-5° C., and 53.74 g. (433 mmoles) of 4-fluorobenzaldehyde is added portionwise, the temperature of the reaction mixture rising to 20° C. during the addition. The solidified reaction mixture is kept at 20°-25° C. for 3 hours and refrigerated for 16 hours. The solid is collected by filtration, rinsed with about 2 l. of water until the rinses are neutral, rinsed with 200 ml. of cold 95% ethanol and recrystallized from 95% ethanol to obtain the product as yellow flakes (66.25 g. (68%)), m.p. 83°-86° C.

Step 2 (Reaction CE)

Ethyl (±)-2-[1'-(4''-fluorophenyl)-3'-oxo-3'-phenylpropyl]-1,3-dithiolane-2-carboxylate (Compound CXXIV)

The product is obtained from 25.0 g. (110.5 mmoles) of Compound CXXIII and 16 ml. (19.7 g.; 110.5 mmoles) of Compound CV utilizing 17 ml. (12.3 g.; 121.5 mmoles) of diisopropylamine and 73.0 ml. of 1.6M. n-butyllithium/hexane (116.8 mmoles) substantially in accordance with the process of Step 3 of Example 1, the principal difference being that subsequent to the evaporation of the tetrahydrofuran the residue is partitioned between diethyl ether and water. The crude product is obtained as a viscous clear brown liquid (45.86 g. (100%)).

Step 3 (Reaction CF)

Ethyl (±)-2,5-dioxo-3-(4'-fluorophenyl)-5-phenylpentanoate (Compound CXXV)

The product is obtained from 45.86 g. (≦110.5 mmoles) of crude Compound CXXIV from Step 2 utilizing 118 g. (663 mmoles) of N-bromosuccinimide substantially in accordance with the process of Step 4 of Example 1, the principal difference being that the reaction mixture is stirred at 0° C. for 3 hours. The obtained cloudy brown viscous oil is chromatographed on a Waters Prep-500 HPLC utilizing a silica gel column, methylene chloride as the eluant and a flow rate of 300 ml./min. The fractions containing a substantial amount of product are combined and evaporated at reduced pressure to obtain the crude product (16.33 g.).

Step 4 (Reaction CG)

Ethyl 3-(4'-fluorophenyl)-1-(1'-methylethyl)-5-phenyl-1H-pyrrole-2-carboxylate (Compound CXXVII)

The product is obtained from 16.33 g. ($\leq$49.7 mmoles) of crude Compound CXXV from Step 3 and 15 ml. (10.28 g.; 173.95 mmoles) of isopropylamine utilizing 30 ml. of 1.0M. titanium tetrachloride/hexane (30 mmoles) substantially in accordance with the process of Step 5 of Example 1, the principal difference being that the reaction mixture is stirred at 20°-25° C. for 30 minutes prior to being refluxed. The obtained viscous orange oil solidifies upon standing, and the obtained solid is recrystallized from absolute ethanol to obtain the product as white needles (6.25 g. (36%)). A previous batch melted at 97°-100° C.

Step 5 (Reaction AA)

3-(4'-Fluorophenyl)-1-(1'-methylethyl)-5-phenyl-1H-pyrrole-2-methanol (Compound CXXVIII)

The product is obtained from 6.25 g. (17.8 mmoles) of Compound CXXVII utilizing 2.0 g. (53.4 mmoles) of lithium aluminum hydride substantially in accordance with the process of Step 6 of Example 1, the principal difference being that the reaction mixture is stirred at 0° C. for 1 hour and at 20°-25° C. for 2 hours. The obtained white powder is recrystallized from diethyl ether/hexane to obtain the product as a white powder (4.83 g. (88%)).

Step 6 (Reaction AB)

3-(4'-Fluorophenyl)-1-(1'-methylethyl)-5-phenyl-1H-pyrrole-2-carboxaldehyde (Compound CXXIX)

The product is obtained from 9.5 g. (30.7 mmoles) of Compound CXXVIII utilizing 589 mg. (0.61 mmole) of tris(triphenylphosphine)ruthenium(II) chloride and 10.51 g. (61.4 mmoles) of N-methylmorpholine-N-oxide.monohydrate substantially in accordance with the process of Step 7 of Example 1, the principal difference being that the reaction mixture is stirred at 20°-25° C. for just 1 hour. The obtained brown solid is dissolved in diethyl ether, the insoluble material is removed by filtration, the diethyl ether is evaporated at reduced pressure to obtain a white solid, and the white solid is recrystallized from diethyl ether to obtain the product as a white powder (7.43 g.), m.p. 118°-122° C. A second crop is also obtained (0.84 g.).

Step 7 (Reaction AF)

Ethyl (E)-3-[3'-(4''-fluorophenyl)-1'-(1''-methylethyl)-5'-phenyl-1H-pyrrol-2'-yl]prop-2-enoate (Compound CXXX)

The product is obtained from 7.3 g. (24 mmoles) of Compound CXXIX and 7.2 ml. (8.07 g.; 36 mmoles) of triethyl phosphonoacetate utilizing 1.51 g. (37.8 mmoles) of 60% sodium hydride/mineral oil substantially in accordance with the process of Step 8 of Example 1, the principal differences being that the reaction mixture is refluxed for 4 hours and the stirring at 20°-25° C. for 16 hours is omitted. The obtained yellow oil solidifies upon standing, and the resulting solid is recrystallized from diethyl ether/hexane to obtain the product as a yellow powder (6.46 g. (71%)), m.p. 84°-87° C.

Step 8 (Reaction AG)

(E)-3-[3'-(4''-Fluorophenyl)-1'-(1''-methylethyl)-5'-phenyl-1H-pyrrol-2'-yl]prop-2-en-1-ol (Compound CXXXI)

The product is obtained from 6.3 g. (17 mmoles) of Compound CXXX utilizing 45 ml. of 1.5M. diisobutylaluminum hydride/toluene (67.5 mmoles) substantially in accordance with the process of Step 9 of Example 1, the principal difference being that the reaction is carried out at 0° C. for 2 hours. However, the use of a lower reaction temperature, e.g., −78° C., should give a much better yield of the product.

Step 9 (Reaction AH)

(E)-3-[3'-(4''-Fluorophenyl)-1'-(1''-methylethyl)-5'-phenyl-1H-pyrrol-2'-yl]prop-2-en-1-al (Compound CXXXII)

The product is obtained from 200 mg. (0.6 mmole) of Compound CXXXI utilizing 14 mg. (0.015 mmole) of tris(triphenylphosphine)ruthenium(II) chloride and 14 mg. (1.2 mmoles) of N-methylmorpholine-N-oxide.-monohydrate substantially in accordance with the process of Step 10 of Example 1, the principal differences being that no additional N-methylmorpholine-N-oxide.-monohydrate is added, the second batch (14 mg.; 0.015 mmole) of the ruthenium salt is added after 2 hours at 20°-25° C., and 1:1 diethyl ether/hexane is utilized as the eluant in the flash chromatography. The product is obtained as a bright yellow foam.

Step 10 (Reaction A)

Ethyl (±)-(E)-7-[3'-(4''-fluorophenyl)-1'-(1''-methylethyl)-5'-phenyl-1H-pyrrol-2'-yl]-5-hydroxy-3-oxohept-6-enoate (Compound CXXXIII)

The product is obtained from 581 mg. (1.74 mmoles) of Compound CXXXII and 0.44 ml. (454 mg.; 3.48 mmoles) of ethyl acetoacetate utilizing 153 mg. of 60% sodium hydride/mineral oil (3.83 mmoles) and 2.2 ml. of 1.65M. n-butyllithium/hexane (3.63 mmoles) substantially in accordance with the process of Step 11 of Example 1, the principal differences being that the reaction mixture is stirred at −20°-−15° C. for 15 minutes prior to the addition of the n-butyllithium/hexane and for just 10 minutes subsequent to the addition of Compound CXXXII, and 60% diethyl ether/hexane is used as the eluant in the flash chromatography. The product is obtained as a viscous yellow oil (545.3 mg.).

The product is a racemate that may be resolved by conventional means to obtain the 5R and 5S enantiomers.

Step 11 (Reaction B)

Ethyl (E)-3,5-dihydroxy-7-[3'-(4"-fluorophenyl)-1'-(1"-methylethyl)-5'-phenyl-1H-pyrrol-2'-yl]hept-6-enoate (Compound CXXXIV)

(a) 1.18 ml. of 1.0M. tri-n-butylborane/tetrahydrofuran (1.18 mmoles) is quickly added dropwise to a solution of 273.2 mg. (0.59 mmole) of Compound CXXXIII in 5 ml. of dry tetrahydrofuran (distilled from ketyl) stirred at 20°–25° C., air is bubbled into the reaction mixture for 1 minute, the reaction mixture is stirred at 20°–25° C. for 1 hour and cooled to −78° C., 56 mg. (1.475 mmoles) of sodium borohydride is added with stirring at −78° C., the reaction mixture is stirred at −50° C. for 16 hours, an additional 56 mg. (1.475 mmoles) of sodium borohydride is added with stirring at −50° C., and the reaction mixture is allowed to slowly warm to −10° C. and is stirred at −10° C. for 1 hour, the reaction mixture being maintained under dry nitrogen throughout. The reaction mixture is quenched at −10° C. with 10% hydrochloric acid (to pH 2), warmed to 20°–25° C. and partitioned between diethyl ether and water, and the aqueous phase is extracted with diethyl ether. The diethyl ether phases are combined, washed twice with saturated sodium chloride solution, dried over anhydrous magnesium sulfate, filtered and evaporated at reduced pressure to obtain the cyclic boron ester as a clear yellow liquid.

(b) The cyclic boron ester product of Part (a) is dissolved in methanol with gentle heating and the methanol is evaporated at reduced pressure, this process is repeated twice more, and the obtained yellow oil is dissolved in the minimum amount of methylene chloride and flash chromatographed on 150 g. of 230–400 mesh A.S.T.M. silica gel utilizing 80% diethyl ether/hexane and then diethyl ether as the eluants. Evaporation of the eluant yields the product as a clear geen oil (166.1 mg.).

N.M.R. (CDCl$_3$): 1.28 (t, 3H), 1.50 (d, 6H), 1.60 (m, 2H), 2.48 (m, 2H), 3.28 (m, 1H), 3.71 (m, 1H), 4.20 (m, 3H), 4.46 (m, 1H), 4.59 (m, 1H), 5.56 (dd, (J$_1$=15 Hz., J$_2$=5 Hz.), 1H), 6.14 (s, 1H), 6.75 (d, (J=15 Hz.), 1H), 7.00 (t, 2H), 7.39 (m, 7H)

The product is a mixture of the erythro and threo racemates wherein the ratio of the former to the latter is about 3:1, which mixture may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a non-stereoselective reduction would afford a mixture of all four stereoisomers wherein the ratio of the erythro stereoisomers to the threo stereoisomers ranges from 3:2 to 2:3.

EXAMPLE 4

Ethyl (±)-erythro-(E)-3,5-dihydroxy-7-[3'-(4"-fluorophenyl)-1'-(1"-methylethyl)-5'-phenyl-1H-pyrrol-2'-yl]hept-6-enoate

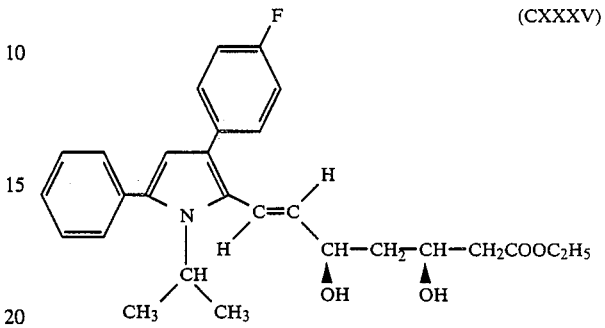

(CXXXV)

A mixture of 120.4 mg. (0.26 mmole) of Compound CXXXIV, 24 mg. (0.39 mmole) of boric acid and 5 ml. of isopropanol is stirred at 80° C. for 3 hours, cooled to 20°–25° C. and evaporated at reduced pressure to obtain a yellow oil. The yellow oil is dissolved in isopropanol with warming, the isopropanol is evaporated at reduced pressure to obtain a yellow foam, the yellow foam is dissolved in the minimum amount of hot isopropanol, the solution is stored at 0° C. for 16 hours, and the mother liquor is decanted. The residual yellow wax is dissolved in methanol with gentle heating and the methanol is evaporated at reduced pressure and this process is repeated twice to obtain a clear yellow oil. The oil is crystallized from methylene chloride/hexane to obtain the product as a flocculant white solid (29.5 mg.), m.p. 105°–107° C.

The product is a mixture of the erythro and threo racemates wherein the ratio of the former to the latter exceeds 9:1, which mixture may be separated by conventional means. The principal product, the erythro racemate, may be resolved into two optically pure enantiomers, the 3R,5S and 3S,5R enantiomers, of which the former is preferred.

EXAMPLE 5

Sodium (±)-erythro-(E)-3,5-dihydroxy-7-[3'-(4"-fluorophenyl)-1'-(1"-methylethyl)-5'-phenyl-1H-pyrrol-2'-yl]hept-6-enoate

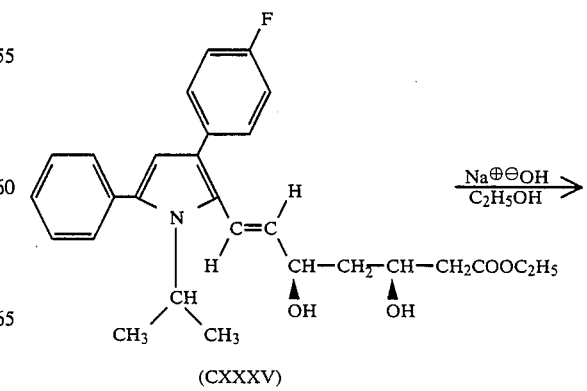

(CXXXV)

-continued

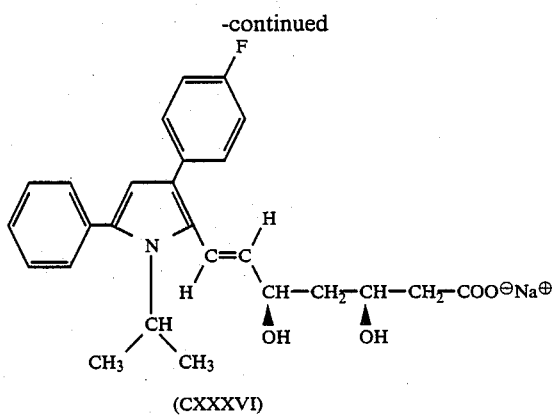

(CXXXVI)

0.08 ml. of 0.5N. sodium hydroxide solution (0.04 mmole) is added dropwise to a solution of 20 mg. (0.043 mmole) of Compound CXXXV in 2 ml. of absolute ethanol stirred at 20°–25° C., the reaction mixture is stirred at 20°–25° C. for 2 hours, the ethanol is evaporated at reduced pressure, the residue is dissolved in water, and the obtained solution is extracted with diethyl ether and lyophilized for 16 hours to obtain the product as a white powder (16.8 mg.), m.p. 185°–192° C. (dec.) (changes color at 135° C.)

N.M.R. (CD$_3$OD+CDCl$_3$): 1.48 (m, 6H), 1.64 (m, 2H), 2.30 (m, 2H), 4.00 (m, 1H), 4.34 (m, 1H), 4.55 (m, 1H), 5.50 (dd (J$_1$=15 Hz., J$_2$=7.5 Hz.), 1H), 6.02 (s, 1H), 6.71 (d (J=15 Hz.), 1H), 7.00 (t, (J=10 Hz.), 2H), 7.38 (m, 7H)

The product is a mixture of the erythro and threo racemates wherein the ratio of the former to the latter exceeds 9:1, which mixture may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a starting material synthesized by using a non-stereoselective reduction in Step 11 of Example 3 would afford a mixture of all four stereoisomers wherein the ratio of the erythro stereoisomers to the threo stereoisomers ranges from 3:2 to 2:3.

Throughout the specification, the term "reduced pressure" denotes aspirator pressure. Where no solvent is specified in connection with a solution, the solvent is water, and all solvent mixtures are by volume. When a reaction is carried out under nitrogen, dry nitrogen is used to maintain anhydrous conditions (except where the reaction medium contains water).

All nuclear magnetic resonance spectra were taken at ambient temperature on a 200 MHz. spectrometer. All chemical shifts are given in p.p.m. (δ) relative to tetramethylsilane, and where a single δ value is given for anything other than a sharp singlet, it is its center point. In the N.M.R. data:
  d=doublet
  dd=doublet of a doublet
  m=multiplet
  s=singlet
  t=triplet Each of the compounds of the examples wherein Z is a group of Formula a wherein R$_{18}$ is a cation may be converted into the corresponding compounds wherein R$_{18}$ is hydrogen or a different cation M, particularly the latter, especially M′, by the processes set forth in Reaction Scheme IV.

Each of the compounds of Examples 1–5 (including each of the possible isomers of the examples) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

What is claimed is:

1. A compound of the formula

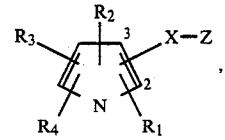

wherein R$_1$ is C$_{1-6}$alkyl not containing an asymmetric carbon atom, C$_{3-7}$cycloalkyl or

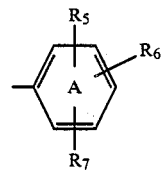

R$_2$ is C$_{1-6}$alkyl not containing an assymetric carbon atom, C$_{3-7}$cycloalkyl or

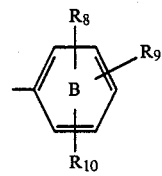

R$_3$ is hydrogen, C$_{1-6}$alkyl not containing an asymmetric carbon atom, C$_{3-7}$cycloalkyl or

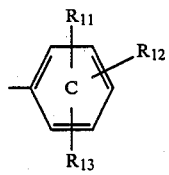

R$_4$ is hydrogen, C$_{1-6}$alkyl not containing an asymmetric carbon atom, C$_{3-7}$cycloalkyl or

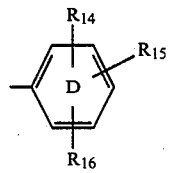

X is —(CH$_2$)$_m$—, —CH=CH—, —CH=CH—CH$_2$— or —CH$_2$—CH=CH—, wherein m is 0, 1, 2 or 3, and Z is

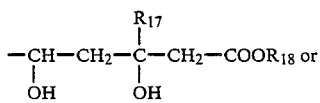

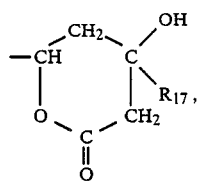

wherein $R_{17}$ is hydrogen or $C_{1-3}$alkyl, and
$R_{18}$ is hydrogen, $R_{19}$ or M, wherein $R_{19}$ is a physiologically acceptable ester group, and
M is a cation,
wherein each of $R_5$, $R_8$, $R_{11}$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_6$, $R_9$, $R_{12}$ and $R_{15}$ is independently hydrogen, $C_{1-3}$alkyl, $C_{1-3}$alkoxy, trifluoromethyl, fluoro, chloro, bromo, phenoxy or benzyloxy, and each of $R_7$, $R_{10}$, $R_{13}$ and $R_{16}$ is independently hydrogen, $C_{1-2}$alkyl, $C_{1-2}$alkoxy, fluoro or chloro, with the provisos that not more than one substituent on each of Rings A, B, C and D independently is trifluoromethyl, not more than one substituent on each of Rings A, B, C and D independently is phenoxy, and not more than one substituent on each of Rings, A, B, C, and D independently is benzyloxy, with the provisos that (i) the —X—Z group is in the 2- or 3-position of the pyrrole ring, (ii) the —X—Z group is ortho to both $R_1$ and $R_2$, and (iii) $R_3$ is ortho to $R_2$.

2. A compound according to claim 1 wherein M is a pharmaceutically acceptable cation.

3. A compound according to claim 2 wherein $R_{19}$ is a physiologically acceptable and hydrolyzable ester group.

4. A compound according to claim 3 wherein $R_{19}$ is $C_{1-3}$alkyl, n-butyl, i-butyl, t-butyl or benzyl.

5. A compound according to claim 2 having the formula

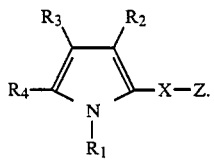

6. A compound according to claim 5 wherein Z is

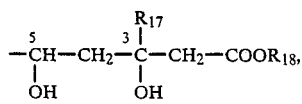

wherein $R_{17}$ is hydrogen or $C_{1-3}$alkyl, and
$R_{18}$ is hydrogen, $R_{19}'$ or M, wherein $R_{19}'$ is $C_{1-3}$alkyl, n-butyl, i-butyl, t-butyl or benzyl, and
M is a pharmaceutically acceptable cation.

7. A compound according to claim 6 wherein $R_1$ is

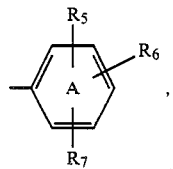

$R_2$ is $C_{1-6}$alkyl not containing an asymmetric carbon atom,
$R_3$ is hydrogen or $C_{1-6}$alkyl not containing an asymmetric carbon atom,
$R_4$ is

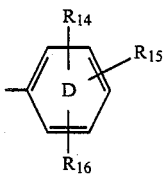

$R_{17}$ is hydrogen or methyl,
$R_{18}$ is hydrogen, $R_{19}'$ or M, wherein $R_{19}'$ is $C_{1-3}$alkyl, n-butyl, i-butyl, t,butyl or benzyl, and
M is a pharmaceutically acceptable cation, and
X is —$CH_2CH_2$— or —CH=CH—,
wherein each of $R_5$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_6$ and $R_{15}$ is independently hydrogen, $C_{1-3}$alkyl, $C_{1-3}$alkoxy, trifluoromethyl, fluoro, chloro, bromo, phenoxy or benzyloxy, and each of $R_7$ and $R_{16}$ is independently hydrogen, $C_{1-2}$alkyl, $C_{1-2}$alkoxy, fluoro or chloro, with the provisos that not more than one substituent on each of Rings A and D independently is trifluoromethyl, not more than one substituent on each of Rings A and D independently is phenoxy, and not more than one substituent on each of Rings A and D independently is benzyloxy.

8. A compound according to claim 7 wherein $R_2$ is $C_{1-4}$alkyl not containing an asymmetric carbon atom,
$R_3$ is hydrogen or $C_{1-2}$alkyl, each of $R_5$ and $R_{14}$ is independently hydrogen, $C_{1-3}$alkyl, $C_{1-2}$alkoxy, trifluoromethyl, fluoro or chloro, each of $R_6$ and $R_{15}$ is independently hydrogen, $C_{1-2}$alkyl, fluoro or chloro each of $R_7$ and $R_{16}$ is independently hydrogen or methyl,
$R_{17}$ is hydrogen,
$R_{18}$ is hydrogen, $C_{1-3}$alkyl or M, wherein M is a pharmaceutically acceptable cation, and
X is (E)—CH=CH—.

9. A compound according to claim 8 wherein $R_3$ is hydrogen or methyl, each of $R_5$ and $R_{14}$ is independently hydrogen, methyl or fluoro, each of $R_6$ and $R_{15}$ is independently hydrogen or methyl,
$R_7$ is hydrogen,
$R_{16}$ is hydrogen, and
$R_{18}$ is hydrogen, $C_{1-2}$alkyl or M, wherein M is a pharmaceutically acceptable cation.

10. A compound according to claim 9 wherein the hydroxy groups in the 3- and 5-positions have the erythro configuration.

11. A compound according to claim 10 having the formula

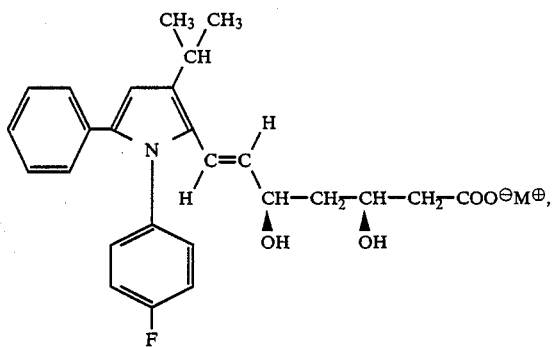

wherein M⊕ is a pharmaceutically acceptable cation.

12. The compound according to claim 11 wherein M⊕ is sodium.

13. A compound according to claim 5 wherein Z is

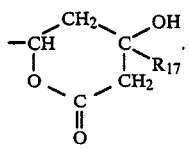

14. A compound according to claim 2 having the formula

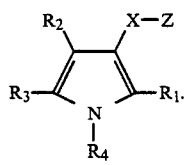

15. A compound according to claim 2 wherein X is —CH=CH—, —CH=CH—CH₂— or —CH₂—CH=CH—.

16. A compound according to claim 15 wherein X is —CH=CH—.

17. A compound according to claim 16 wherein X is (E)—CH=CH—.

18. A pharmaceutical composition comprising an effective amount of a compound according to claim 2 and a pharmaceutically acceptable carrier, said effective amount being an amount effective for inhibiting cholesterol biosynthesis in a mammal.

19. A method of inhibiting cholesterol biosynthesis comprising administering to a mammal in need of such treatment an effective amount of a compound according to claim 2, said effective amount being an amount effective for inhibiting cholesterol biosynthesis.

20. A method of treating atherosclerosis comprising administering to a mammal in need of such treatment an effective amount of a compound according to claim 2, said effective amount being an amount effective for the treatment of atherosclerosis.

21. A method of treating atherosclerosis according to claim 20 comprising administering to a mammal in need of such treatment an effective amount of a compound of the formula

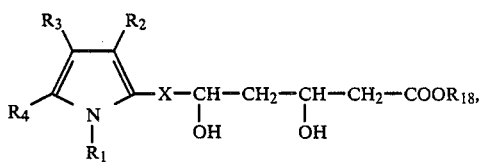

said effective amount being an amount effective for the treatment of atherosclerosis.

22. A method of treating atherosclerosis according to claim 21 comprising administering to a mammal in need of such treatment an effective amount of a compound of the formula

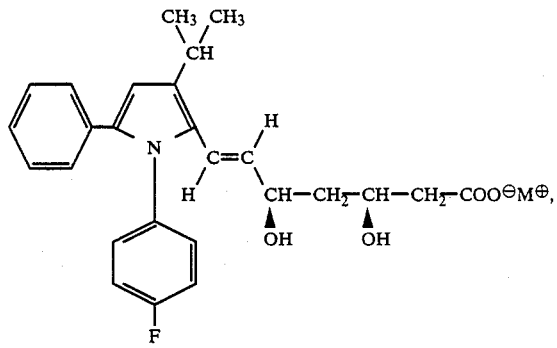

* * * * *